(12) United States Patent
Hendrick et al.

(10) Patent No.: US 11,806,107 B2
(45) Date of Patent: Nov. 7, 2023

(54) PHYSICIAN INPUT DEVICE FOR A CONCENTRIC TUBE SURGICAL ROBOT

(71) Applicant: Virtuoso Surgical, Inc., Nashville, TN (US)

(72) Inventors: Richard Hendrick, Nashville, TN (US); Neal Dillon, Nashville, TN (US); Lauren Branscombe, Nashville, TN (US); Evan Blum, Nashville, TN (US); Stephanie Amack, Nashville, TN (US)

(73) Assignee: Virtuoso Surgical, Inc., Nashville, TN (US)

(*) Notice: Subject to any disclaimer, the term of this patent is extended or adjusted under 35 U.S.C. 154(b) by 548 days.

(21) Appl. No.: 17/113,892

(22) Filed: Dec. 7, 2020

(65) Prior Publication Data

US 2022/0175482 A1 Jun. 9, 2022

(51) Int. Cl.
*A61B 34/00* (2016.01)
*A61B 90/00* (2016.01)
*A61B 34/30* (2016.01)
*A61B 46/10* (2016.01)
*G05B 19/427* (2006.01)
(Continued)

(52) U.S. Cl.
CPC ............... *A61B 34/74* (2016.02); *A61B 34/30* (2016.02); *A61B 46/10* (2016.02); *A61B 90/06* (2016.02); *G05B 19/427* (2013.01); *G06F 3/011* (2013.01); *A61B 1/00149* (2013.01); *A61B 34/76* (2016.02); *A61B 2034/301* (2016.02); *A61B 2034/742* (2016.02); *A61B 2090/061* (2016.02); *A61B 2090/067* (2016.02); *G06F 3/04847* (2013.01)

(58) Field of Classification Search
CPC ......... A61B 34/74; A61B 34/30; A61B 46/10; A61B 1/00149; A61B 34/76; A61B 2034/301; A61B 2034/742; A61B 1/00042; A61B 34/37; G05B 19/427; G06F 3/011
See application file for complete search history.

(56) References Cited

U.S. PATENT DOCUMENTS

2018/0028054 A1  2/2018  Hoffman et al.
2019/0090971 A1  3/2019  Peine
(Continued)

OTHER PUBLICATIONS

PCT/US2021/062220, International Search Report and Written Opinion, dated Apr. 11, 2022, 9 pages.

*Primary Examiner* — Julian W Woo
(74) *Attorney, Agent, or Firm* — Holland & Knight LLP; Matthew C. Cox

(57) ABSTRACT

A highly intuitive physician input device for communication with a minimally invasive endoscopic concentric tube surgical robot. The physician input device can comprise a user interface handle assembly, a user interface linear joint assembly, a user interfaced bearing block assembly, and a user interface base assembly, and sensors distributed throughout to measure each of these axes, possibly redundantly for safety. Due to the network of sensors and encoders built in to the physician input device, it is capable of triggering a movement in the endoscopic concentric tube robot corresponding to that of the movements made on the physician input device. There are at least four movement controls the physician input device is capable of communicating to the concentric tube robot, those being translation, pan, tilt, and axial rotation. In some embodiments a fifth control includes actuation of a tool such as a gripper.

23 Claims, 23 Drawing Sheets

(51) Int. Cl.
*G06F 3/01* (2006.01)
*G06F 3/04847* (2022.01)
*A61B 1/00* (2006.01)

(56) References Cited

U.S. PATENT DOCUMENTS

| | | |
|---|---|---|
| 2019/0328473 A1 | 10/2019 | Chassot et al. |
| 2020/0289229 A1 | 9/2020 | Denlinger et al. |
| 2020/0352658 A1 | 11/2020 | Johnson et al. |
| 2021/0393338 A1* | 12/2021 | Graetzel ................ A61B 34/20 |

* cited by examiner

PHYSICIAN INPUT DEVICE FOR A CONCENTRIC TUBE SURGICAL ROBOT

STATEMENT REGARDING FEDERAL SPONSORED RESEARCH

This invention was made with government support under R44HL140709 and R44EB024423 awarded by National Institutes of Health. The government has certain rights in the invention.

CROSS-REFERENCES TO RELATED APPLICATIONS

None.

BACKGROUND

The present subject matter relates generally to robotic endoscopy surgical instruments and associated methods for performing precision surgery. More particularly, the present invention relates to an input device that enables doctors to accurately move and control an endoscopic concentric tube robotic surgery system.

Over the past few decades, it has become increasingly clear that entering the body in the most minimally invasive way possible during surgery provides tremendous patient benefit. Minimally invasive surgery is a general term used to describe any surgical procedure that enters the body without large, open incisions. Conventional devices for performing minimally invasive surgery, such as endoscopes and resectoscopes, are generally rigid and include a distal tip that is inserted through an incision in a patient's body or a natural orifice in a patient's body. The distal tip includes an optical lens which allows a surgeon to see a field of view proximate to the distal tip when placed inside the body. The endoscope will typically have a camera attached to it to display the field of view on an operating room monitor. In some applications the endoscope includes a camera installed on the distal tip of the endoscope. The device also includes a working channel extending through the device. One or more elongated surgical tools may be inserted through the working channel. A tool such as a cutting device, a basket or a laser optic may be included on the surgical tool. The distal end of the surgical tool protrudes from the distal tip of the device, thereby allowing the surgeon to visually observe operation of the tool inside the patient's body during an operation.

Minimally invasive surgery includes laparoscopic surgery, which uses a tube to deliver visualization (i.e. an endoscope) and view the surgical field and long, rigid instruments that pass through small ports in the body. In conventional laparoscopic surgery, the endoscope is usually used only for visualization of the surgical field and does not have tools passing through it. The tools are pivoted outside of the body and through the incision port to provide instrument manipulation at the surgical site. The tool manipulation in laparoscopic surgery is created by pivoting long, rigid shafts through ports in the body. For surgery in the insufflated abdomen, chest cavity, pelvis or any other anatomical working volume with sufficient space, this concept often provides an excellent minimally invasive solution for delivering instrument manipulation. However, when the surgical site is down a long, narrow channel, the ability to pivot these long, rigid shafts diminishes. The tool's manipulation ability drops off sharply as access channels become longer and/or narrower.

Minimally invasive surgery also includes endoscopic surgery. While laparoscopic surgery uses endoscopes to provide visualization, endoscopic surgery differs in that the surgical instruments are passed through a working channel of the endoscope tube itself. Some examples of surgical instruments that can be used during endoscopic surgery are scissors, forceps, laser fibers, and monopolar/bipolar cautery. There are both rigid and flexible endoscopes—rigid endoscopes being used in surgeries where a straight, linear path can be taken from the outside of the body to the surgical site, and flexible endoscopes being used where winding through curving anatomy is required. Rigid endoscopes are currently used in almost every area of surgery, including but not limited to neurologic, thoracic, orthopedic, urologic and gynecologic procedures. While rigid endoscopy is currently used in surgeries all over the body, it is not without drawbacks. Tools that operate through the working channel of rigid endoscopes are similar to laparoscopic tools in that they are normally straight, rigid tools. Generally, these tools are also limited to two degrees-of-freedom motion relative to the endoscope: they can insert/retract and rotate axially. Sometimes, the surgeon may have the ability to pivot/tilt the endoscope outside of the body, which makes things particularly challenging, as whenever the endoscope moves, the field of view of the endoscope moves along with it. Also, the surgeon can only get one instrument at a time to the surgical site the vast majority of the time due to the size constraints of the working channel of the endoscope—effectively eliminating the ability for two-handed bimanual tasks. This limitation to a single tool at a time, the constantly changing field of view, limited degrees of freedom, and lack of instrument dexterity at the tip of the endoscope make endoscopic surgery a particularly challenging type of minimally invasive surgery.

Because they are particularly skilled with precision, spatial reasoning, and dexterity, electromechanical surgical robots have great potential to aid in surgical instrument manipulation and is a rapidly developing field of medicine. Surgical robots have gained widespread adoption throughout the world and have been utilized in hundreds of thousands of procedures. The majority of surgical robotic systems designed thus far that aid in instrument manipulation can be generally categorized into pivoted and flexible tools. Pivoted, laparoscopic-like systems such as the widely used da Vinci Xi robot, made by Intuitive Surgical, Inc., gain instrument manipulation in the same way that laparoscopic tools do: by tilting through a port in the body. For surgical applications where tilting or pivoting of the tools is not possible outside of the body, several groups in the research community have been developing robotic systems based on flexible elements. These systems are often referred to as continuum robots, or a continuously bending, robot with an elastic structure. There also exist concentric tube manipulators, which are a class of miniature, needle-sized continuum robot composed of concentric, elastic tubes. Concentric tube robots appear promising in many kinds of minimally invasive surgical interventions that require small diameter robots with articulation inside the body. Examples include surgery in the eye, hear, sinuses, lungs, prostate, brain, and other areas. In most of these applications, higher curvature is generally desirable to enable the robot to turn "tighter corners" inside the human body and work dexterously at the surgical site. In the context of endoscopic surgery, the precurvatures of the concentric tubes determine how closely the manipulators can work to the tip of the endoscope, which is very important during endoscopic surgery.

With traditional endoscopic procedures, surgeons typically hold the endoscope in one hand and the endoscopic instrument in the other, making it generally not possible for the surgeon to simultaneously manipulate two instruments. Due to the human error aspect, whenever the surgeon needs to swap one endoscopic instrument out for another can result in awkward and potentially dangerous endoscope movements. Surgeons often, however, need the ability to accurately and simultaneously manipulate two instruments in certain situations especially when trying to grasp, manipulate, and cut material precisely. Even where endoscopes can accommodate more than one tool simultaneously, the tools can only be oriented straight out and parallel to one another, which prohibits truly collaborative work between the tools. Surgeons can greatly benefit from the increased precision, dexterity, and vision that robotic surgery systems offer, but such conventional systems are limited in their manipulability.

Another problem with conventional surgical robots is that conventional user input consoles are generally not configured for use in the sterile field. Thus, a surgeon operating an input console must be standing outside the surgical suite in a remote, non-sterile environment. This can be inconvenient, especially if the surgeon needs to move back and forth between the sterile field and the user input console during an operation.

Accordingly, there exists a need for new improvements in intuitive, dexterous, and accurate endoscopic robotic surgical systems.

BRIEF SUMMARY

The present disclosure relates generally to physician input devices and systems for robotically performing minimally invasive surgery. In some embodiments, the present invention includes an endoscopic surgical system that delivers two robotically controlled concentric tube manipulators that work to perform surgery from the tip of a rigid endoscope. In some embodiments, a surgeon may maneuver the joystick-like handles of a physician input device to control a corresponding movement in one or both of the independently movable robotic concentric tube manipulators protruding from the tip of a rigid endoscope element.

In some embodiments, an objective of the present disclosure is to provide a system that replaces straight tools in almost any rigid endoscopic procedure and enables the surgeon to grasp, manipulate, and cut tissue with a dexterity and precision unparalleled in conventional rigid endoscopy.

Another objective of the present disclosure is to provide a physician input device for controlling a tube in a concentric tube array using a handheld controller with a tilt degree of freedom and a linear in/out degree of freedom to control corresponding tilt and linear motion of the inner tube in a patient. In additional embodiments, a third degree of freedom with side-to-side pan is provided. A fourth degree of freedom includes rotation about a longitudinal axis in some embodiments.

Another objective of the present disclosure is to provide a physician input device that a surgeon can use to safely control an endoscopic tool during the course of a surgical procedure using a rigid endoscope and having the benefit of a camera lens mounted thereon for viewing a workspace in real time. The endoscope camera can be in communication with an operating room monitor for live visual, endoscopic feedback of the internal surgical site that the surgeon can observe while performing surgery. The endoscopic element can deliver two robotically controlled, concentric tube manipulator arms and an optical lens mounted above them. In particular, the concentric tube arms can be made from nitinol, due to its large recoverable strain and its ability to be shape set into desired curves while maintaining its superelasticity. The manipulators at the end of the concentric tube arms can comprise a number of surgical tools, including but not limited to graspers, forceps, knives, brushes, scalpels, biopsy devices, electrocautery devices, and tissue scissors and cutters.

A further objective of the present disclosure is to provide a physician input device that robotically controls concentric tubes of an endoscopic surgical robot in a highly safe and intuitive manner.

Another objective of the present disclosure is to provide a physician input device configured for controlling a surgical robot that can be located in the sterile field during a surgical procedure. In some embodiments, the present disclosure provides a physician input device with user inputs configured such that they may be operated by a surgeon who is scrubbed in at or near the sterile field using one or more drapes, or alternatively may be used outside the sterile field in a remote environment.

Numerous other objects, advantages and novel features of the present invention will be readily apparent to those skilled in the art upon a reading of the following disclosure when taken in conjunction with the accompanying drawings and the claims.

DETAILED DESCRIPTION

Figure 1:
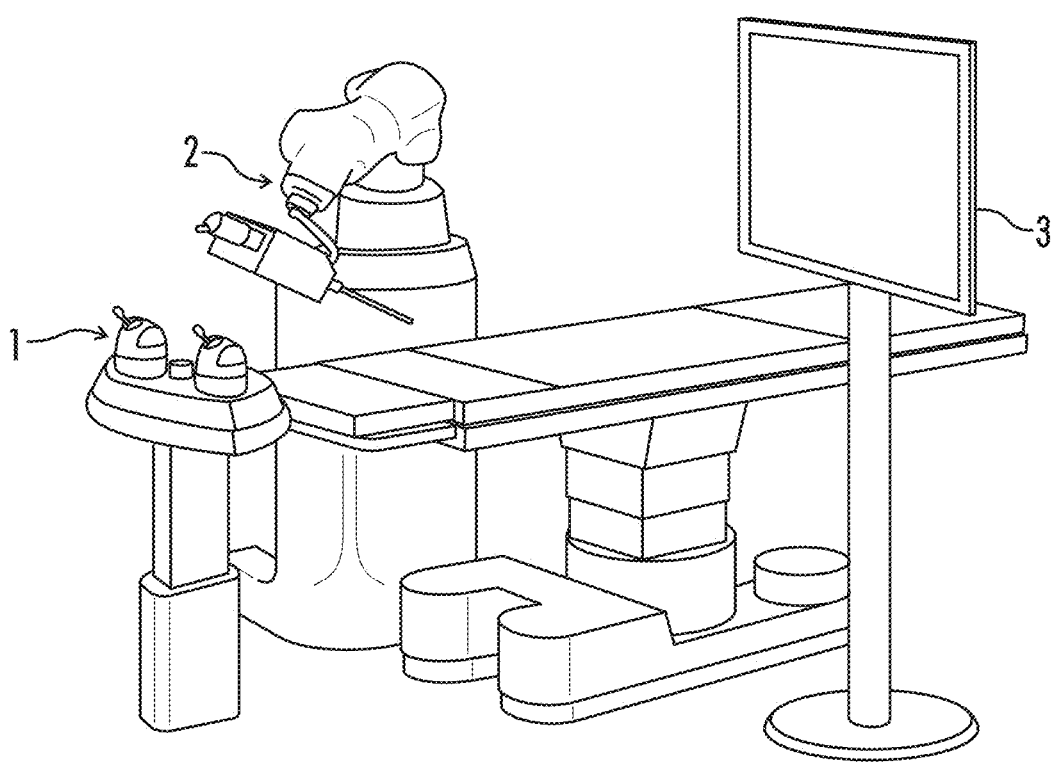
FIG. 1 illustrates a general perspective view of an embodiment of the endoscopic concentric tube robot-assisted precision surgical system.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

Referring now to the drawings, various views of embodiments of devices for performing minimally invasive surgery are illustrated. In the drawings, not all reference numbers are included in each drawing, for the sake of clarity. The devices shown in the illustrations are not intended to illustrate all possible embodiments of the claimed invention, but are rather included as examples. A person of skill in the art will understand the devices and methods of the claimed invention may include different configurations and orientations not shown in the figures.

The present disclosure provides a physician input device for robotically performing minimally invasive surgery. An overview of an embodiment of the endoscopic concentric tube robot-assisted precision surgical system can be seen in FIG. 1, wherein a physician input device 1 is in direct communication with an endoscopic concentric tube robot 2 that is in direct communication with an operating room monitor 3.

Figure 2:
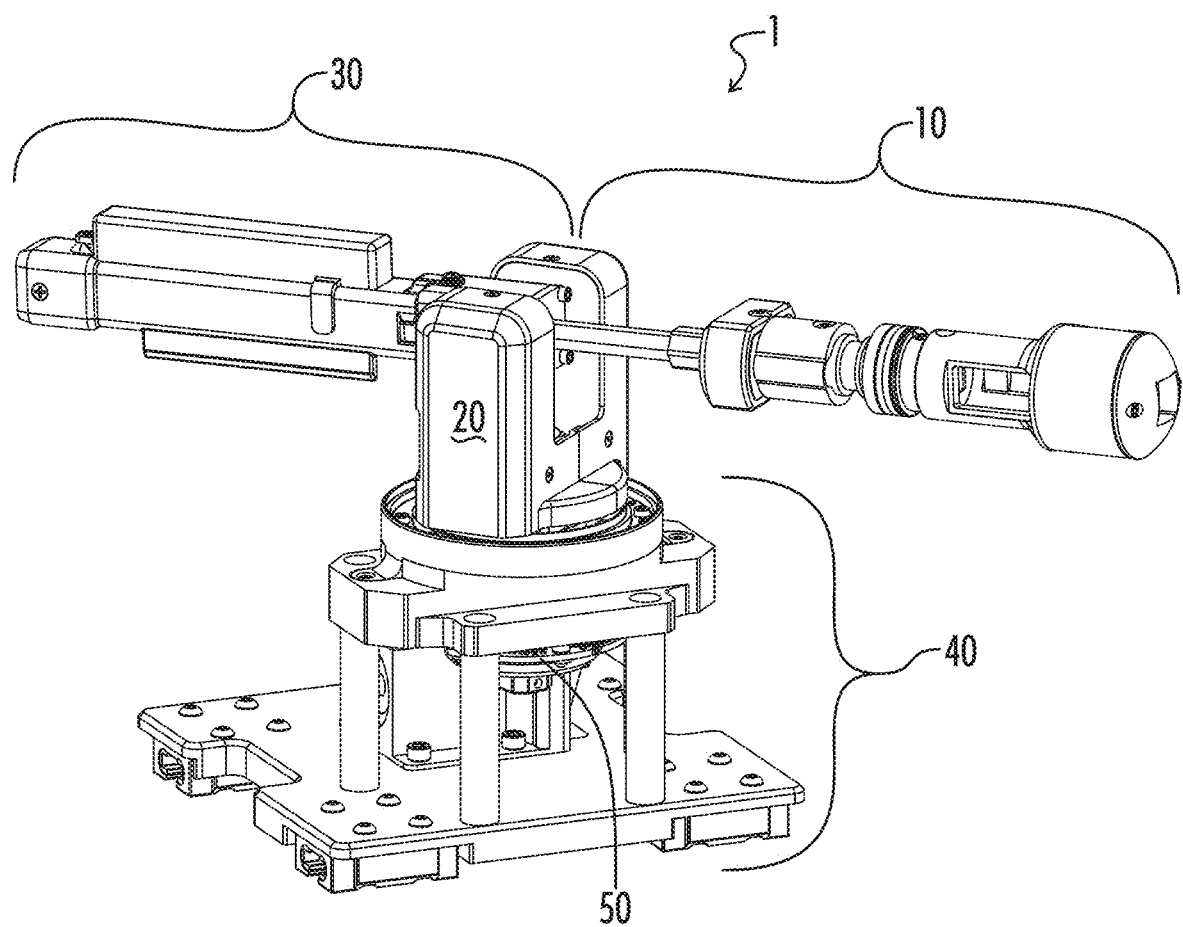
FIG. 2 illustrates a perspective view of an embodiment of a physician input device.

A more detailed view of one embodiment of a physician input device 1 is shown in FIG. 2. The physician input device 1 can comprise a user interface handle assembly 10, a user interface pan/tilt assembly 20, a user interface linear joint assembly 30, a user interface base assembly 40, and a rotary encoder 50. In some embodiments, each of assemblies 10, 20, 30, and 40 can contain various types of sensors that are in communication with one another, continuously tracking every movement of the physician input device 1.

The physician input device includes three degrees of freedom for controlling corresponding movement of a surgical tool on the distal tip of a concentric tube assembly in some embodiments. For example, when in use, certain embodiments of the physician input device 1 can produce (1) a translation movement in the endoscopic concentric tube robot 2 by pulling in or pushing outward the user interface handle assembly 10; (2) a panning movement in the concentric tube robot 2 by moving the user interface handle assembly 10 side to side, left or right; (3) a tilt movement in the concentric tube robot 2 when moving the user interface handle assembly 10 up or down. In further embodiments, a fourth degree of freedom controls (4) an axial rotation movement in the concentric tube robot 2 by axially rotating the user interface assembly 110 portion of the touch point assembly 100.

Figure 2A:
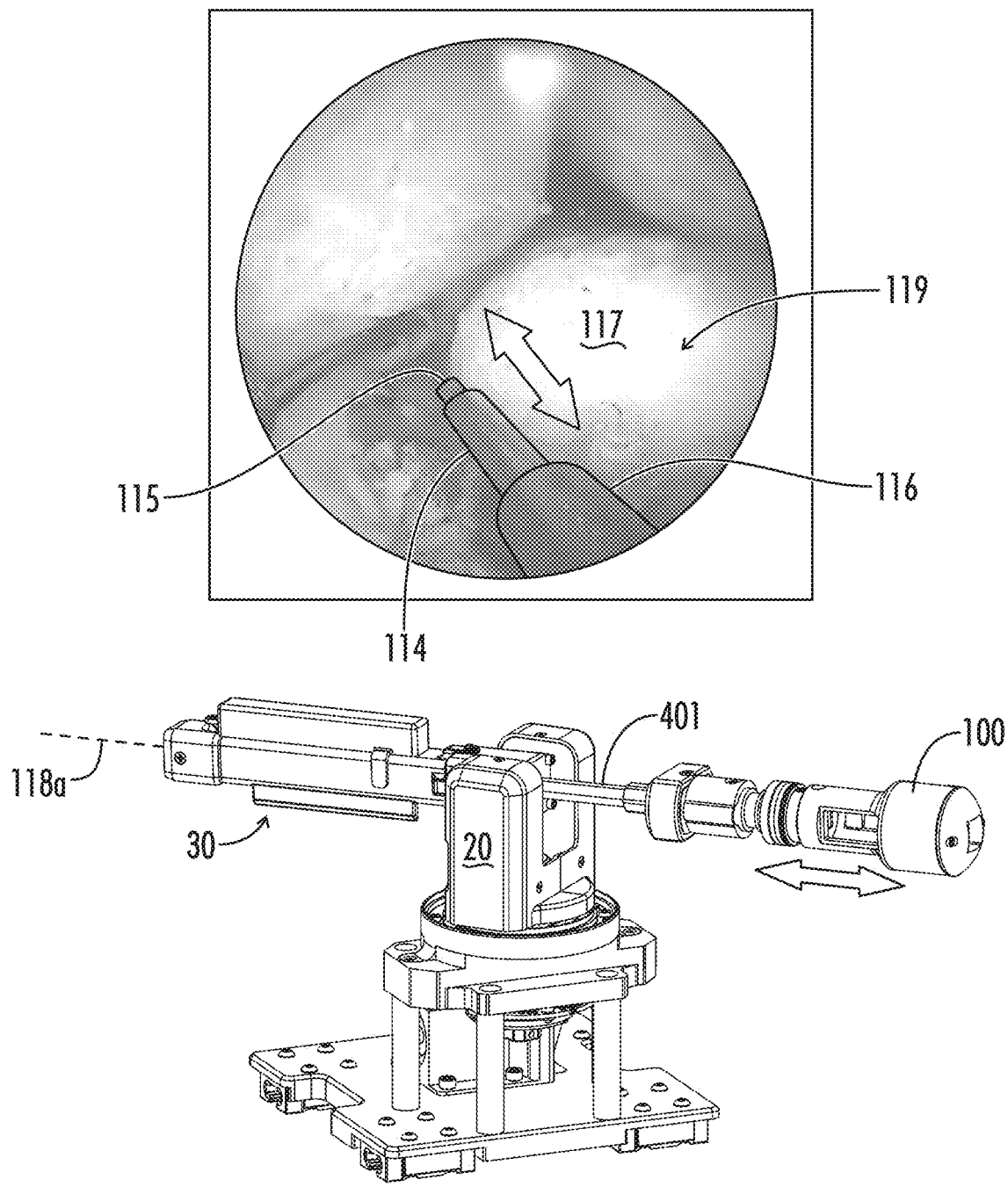
FIG. 2A illustrates a perspective view of an embodiment of a user interface handle assembly and a field of view of a concentric tube assembly showing a translation degree of freedom.

Referring to FIG. 2A, a first degree of freedom includes a linear translation of the touch point assembly 100, or handle, by a user's hand. When the handle is translated forward toward pan/tilt assembly 20 and UI linear joint assembly 30, a translation sensor detects the translation and sends a control signal to a driver coupled to a first tube assembly 119. The first tube assembly 119 includes a guide tube 116 and an inner tube 114 positioned inside the guide tube 116. The inner tube 114 is able to translate longitudinally inside the guide tube 116. The guide tube 116 includes a curved distal tip which steers the inner tube 114 in a desired direction. The guide tube may be rotated in a channel in the endoscope. When the handle on input device 1 is translated linearly along translation axis 118a, inner tube 114 is moved in a corresponding motion such that inner tube 114 translates in or out of the distal tip of guide tube 116 in a linear movement. For example, when handle 100 is pushed inwardly toward UI linear joint assembly 30, a corresponding extension of inner tube 114 relative to guide tube 116 occurs in the tube assembly 119. Similarly, when handle 100 is pulled back by the user along translation axis 118a, a corresponding retraction of inner tube 114 relative to guide tube 116 occurs. By mapping in-and-out translation of handle 100 to corresponding movement of inner tube 114, input device 1 provides a user-friendly and intuitive interface for extending and retracting the tool 115 in a tissue workspace.

Figure 2B:
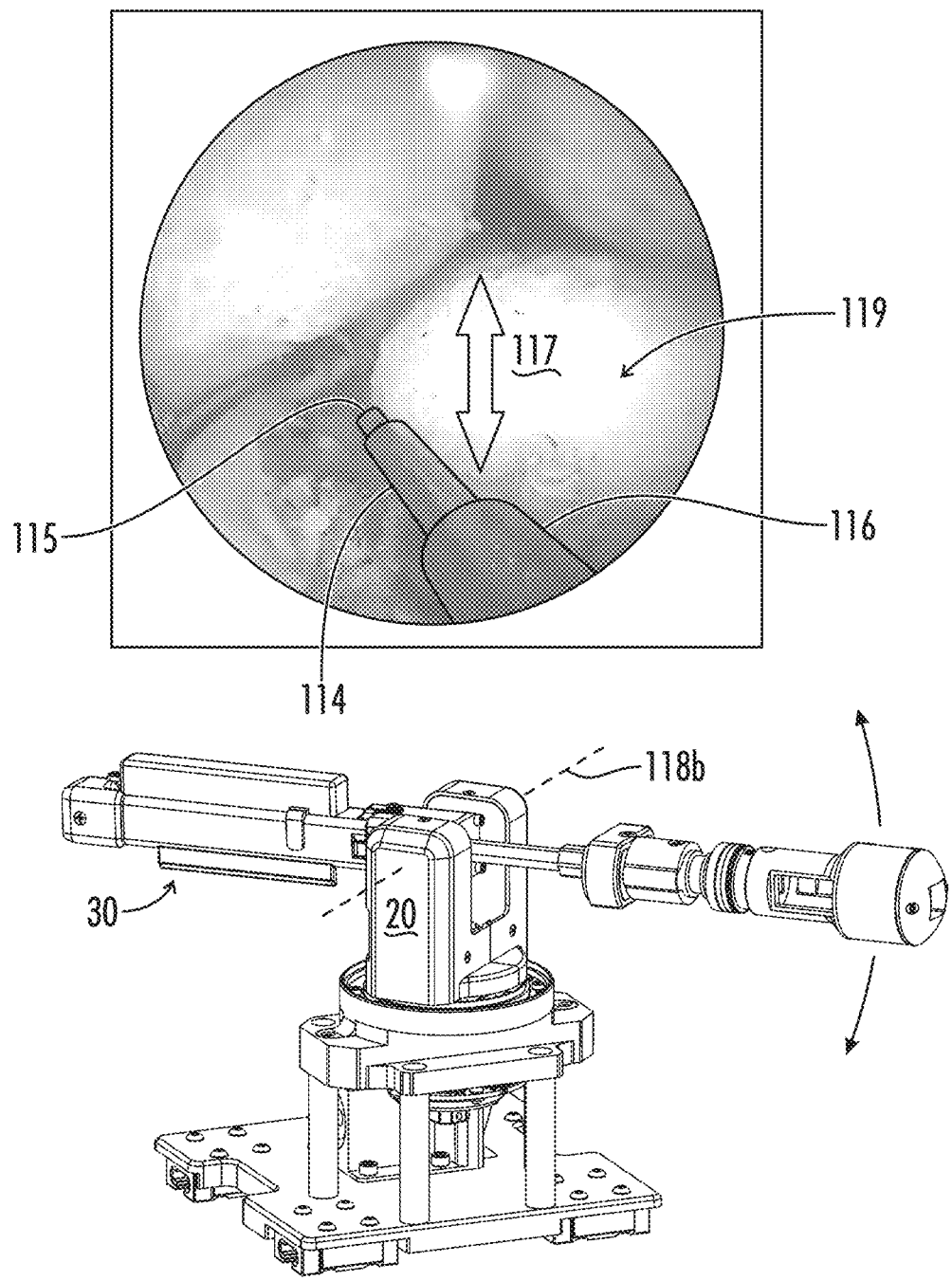
FIG. 2B illustrates a perspective view of an embodiment of a user interface handle assembly and a field of view of a concentric tube assembly showing a tilt degree of freedom.

Referring to FIG. 2B, a second degree of freedom includes an up-and-down tilt feature. When the handle 100 is moved angularly about a horizontal reference axis 118b relative to UI pan/tilt assembly 20, one or more sensors detects the movement and sends a control signal to a driver to impart a corresponding motion on tube assembly 119. For example, as shown in FIG. 2B, when handle 100 is tilted upwardly about horizontal axis 118b, inner tube 114 is translated in a corresponding upward motion in the surgical field of view. Similarly, when handle 100 is tilted downwardly about horizontal axis 118b, inner tube 114 is translated in a corresponding downward motion in the surgical field of view. This allows a user to map movement of the handle 100 directly onto corresponding motion of the inner tube 114 and tool 115 in a tissue workspace.

Some users prefer having a reverse correlation between input direction and tilt motion of the tool in the workspace. Because the correlation between movement of the up-and-down tilt feature on the physician input is mapped to the driver controlling motion of the tube assembly using software and an electronic signal, the apparatus can be provided in a reverse configuration in some embodiments. For example, in a reverse configuration, when handle 100 is tilted angularly upward about a horizontal reference axis 118b relative to UI pan/tilt assembly 20, inner tube 114 is translated in a corresponding downward motion in the surgical field of view. Similarly, in the reverse configuration embodiment, when handle 100 is tilted downwardly about horizontal axis 118b, inner tube 114 is translated in a corresponding upward motion in the surgical field of view.

Figure 2C:
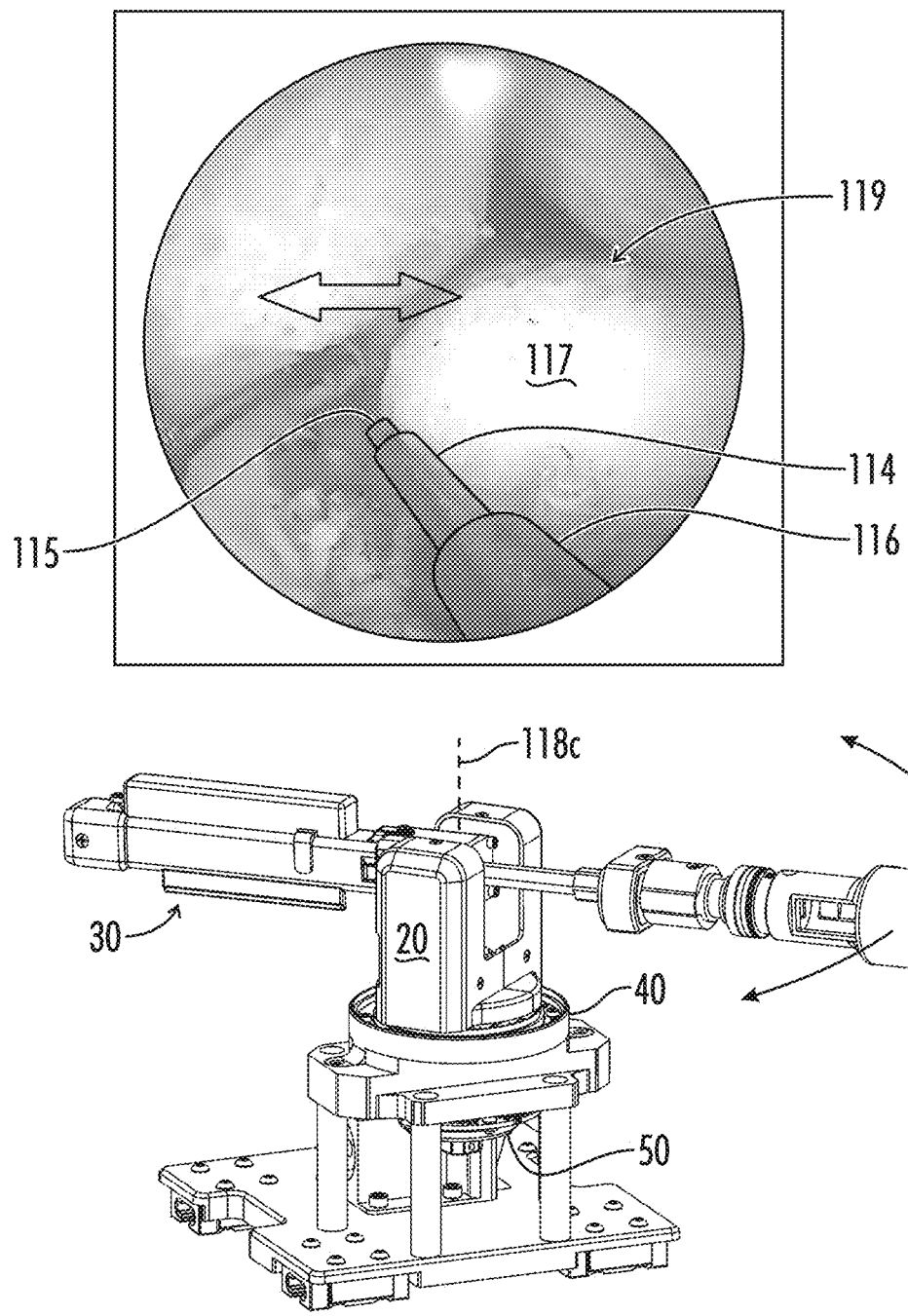
FIG. 2C illustrates a perspective view of an embodiment of a user interface handle assembly and a field of view of a concentric tube assembly showing a pan degree of freedom.

Referring to FIG. 2C, a third degree of freedom includes a side-to-side pan feature. When handle 100 is moved angularly relative to a reference vertical axis 118c, a corresponding movement of tube assembly 119 allows inner tube 114 and tip 115 to sweep from side to side in the field of view. For example, when handle 100 is panned to the left in a pivoting motion about reference vertical axis 118c, an inner tube 114 moves to the left in the field of view in a corresponding motion. Similarly, when handle 100 is moved to the right in a pivoting motion about reference vertical axis 118c, inner tube 114 moves to the right in the field of view in a corresponding motion.

Some users also prefer having an inverse correlation between input direction and side-to-side pan motion of the surgical tool in the workspace. Because the correlation between movement of the side-to-side pan feature on the physician input is mapped to the driver controlling motion of the tube assembly using software and an electronic signal, the apparatus can be provided in a reverse configuration in some embodiments. For example, in a reverse configuration, when handle 100 is panned from right-to-left about a vertical reference axis 118c, inner tube 114 is panned in a corresponding left-to-right motion in the surgical field of view. Similarly, in the reverse configuration embodiment, when handle 100 is panned from left-to-right about vertical reference axis 118c, inner tube 114 is panned in a corresponding right-to-left motion in the surgical field of view.

A fourth degree of freedom provides a rotation feature in some embodiments. When handle 100 is rotated angularly about translation axis 118a, a corresponding roll or rotation occurs in inner tube 114 and tool 115 in the field of view. This feature is desirable when tool 115 includes a gripper device or other tool requiring angular orientation about the longitudinal axis.

In some embodiments, the multiple degrees of freedom are cooperative and may be used simultaneously to control motion of the inner tube 114 in the field of view. For example, a user may simultaneously rotate, tilt, pan and extend or retract the handle 100 to cause a corresponding movement of the inner tube 114 and tool 115 in the field of view. The input device 1 in some embodiments forms a gimbal with three degrees of freedom, including angular pan, angular tilt and linear translation.

Figure 3:
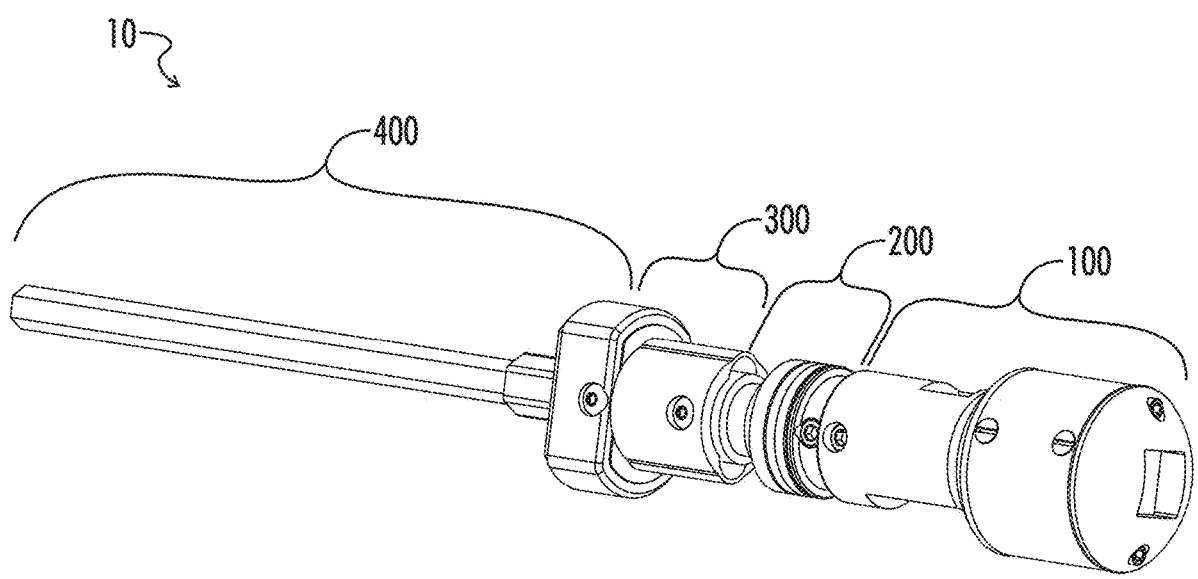
FIG. 3 illustrates a perspective view of the embodiment of a user interface handle assembly in FIG. 2.
Figure 4:
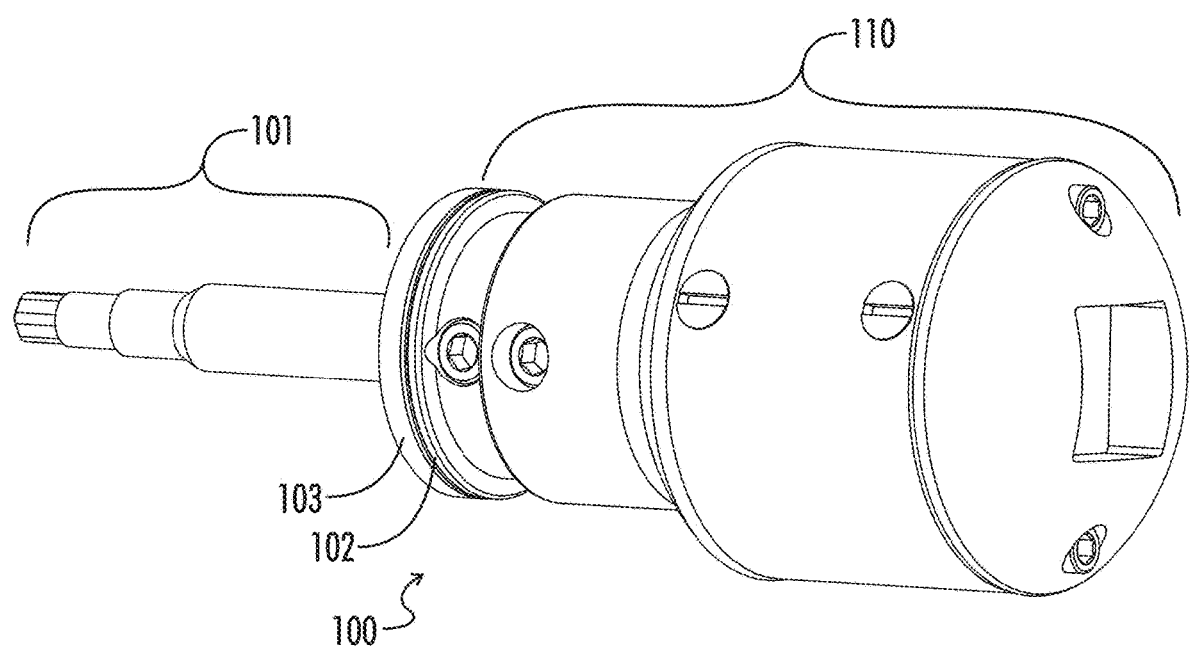
FIG. 4 illustrates a perspective view of the embodiment of a touch point assembly in FIG. 3.

As shown in FIG. 3, one embodiment of a handle assembly may comprise a touch point assembly 100, a handle bearing assembly 200, a magnetic sensor housing assembly 300, and a shaft stem assembly 400, all directly connected to one another. In some embodiments, as shown in FIG. 4, the touch point assembly 100 comprises a touch point shaft 101, a friction gasket 102, a flat washer 103, and a touch-sensitive user interface assembly 110.

In other embodiments, the touch point assembly 100 can additionally comprise at least one touch sensor or a sensor array that is capable of detecting if and when the physician contacts the touch point assembly 100 by hand. In such embodiments, the touch sensors act as a safety mechanism to prevent unintentional movement of the tube assembly. For example, the touch sensor can intervene and prevent a corresponding movement of the endoscopic concentric tube robot 2 in such instances where the input or workstation is accidentally bumped into. Additionally, the touch sensors could be responsible for activating the direct connection between the physician input device 1 and endoscopic concentric tube robot 2 only upon its detection of a set amount of contact points between the physician's hand and the touch point assembly 100.

Figure 5:
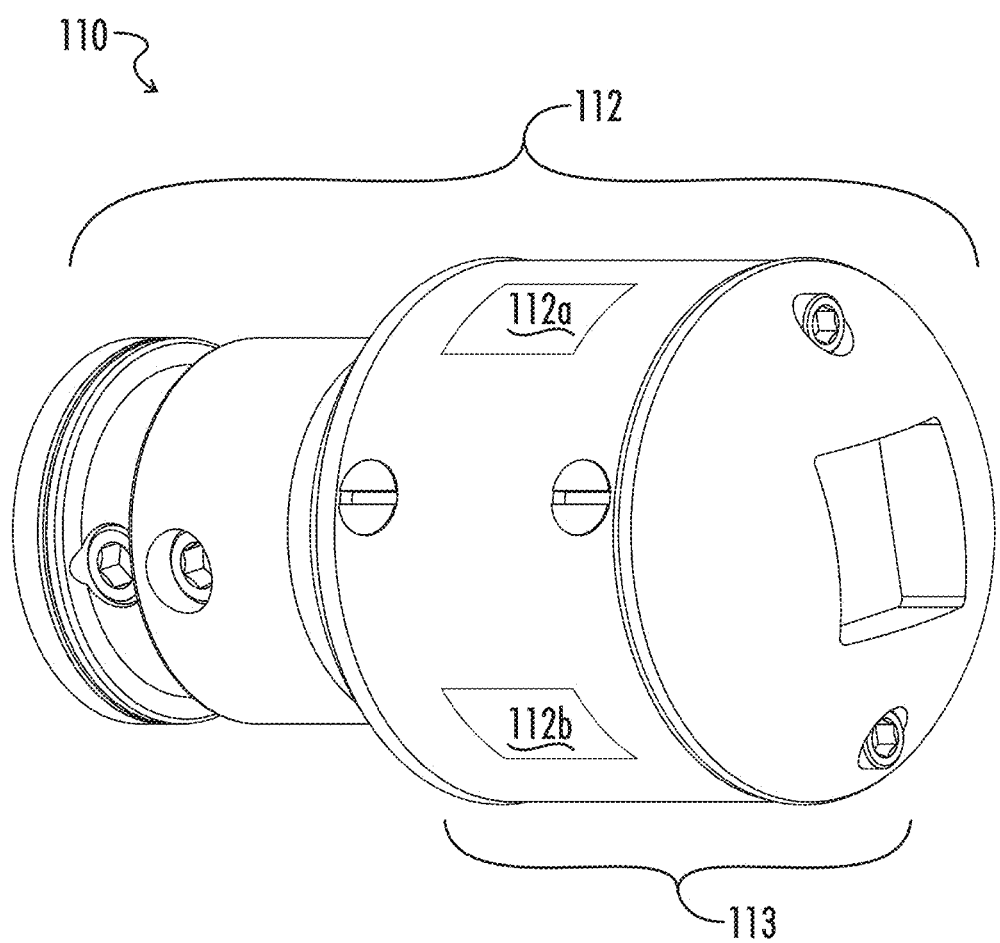
FIG. 5 illustrates a perspective view of the embodiment of a capacitive user interface assembly of FIG. 4.

In one embodiment depicted in FIG. 5, the touch-sensitive user interface assembly 110 portion of the touch point assembly 100 can further comprise a touch point capacitive end cap 111, a touch point capacitive main body 112, and a panel mount 113 that defines a hollow internal portion of the capacitive main body 112. In certain embodiments, the touch point capacitive main body 112 is one of the many areas of the input device 1 that can house one or more touch sensors, which act as safety mechanisms in the manners described above. For example, in some embodiments, a first sensor 112a and a second sensor 112b are positioned on the body 112. The input device is configured to prevent actuation of the tube assembly unless both the first and second sensors 112a, 112b are contacted by a user's hand. First and second sensors can include any suitable sensor known in the art, such as a capacitive touch sensor, a pressure sensor or a switch.

Referring further to FIG. 5, in some embodiments, user interface assembly 110 includes an array of contacts, or pads 112, positioned around the periphery of the handle. Each contact, or pad 112a, 112b, etc. is connected to a central multi-channel sensor. For example, first pad 112a is connected to a first channel on a sensor, second pad 112b is connected to a second channel on the sensor, and additional pads positioned on the handle are each connected to a separate channel on the sensor. In some embodiments, the sensor includes a multi-channel sensor having eight channels, and each channel is connected to a corresponding pad located around the periphery of the handle. The system can be programmed to prohibit movement of the tube array if a pre-determined combination of different pads at different locations is not simultaneously contacted by a user's hand.

Some embodiments of the physician input device and associated methods include redundant sensing along the multiple degrees of freedom to provide additional safety. For example, in some embodiments, the input device 1 includes a first degree of freedom including linear translation along a reference axis 118a. First and second translation sensors both detect linear motion of the handle 100 along reference axis 118a. If the translation data associated with linear translation of handle 100 acquired by both the first and second sensors is not within a predetermined threshold range of similarity, the system may prevent corresponding motion of the tube array in the workspace.

Similar redundancy is provided with respect to each additional axis in some embodiments. For example, first and second tilt sensors positioned on the device detect angular movement of handle 100 up or down relative to reference horizontal axis 118b, shown in FIG. 2B. If the angular position data acquired by each of the first and second sensors is not within a predetermined threshold range of similarity, the system may prevent corresponding motion of the tube array in the workspace. Also, first and second pan sensors positioned on the device detect angular movement of handle 100 side-to-side relative to reference vertical axis 118c, shown in FIG. 2C. If the angular position data acquired by each of the first and second pan sensors is not within a predetermined threshold range of similarity, the system may prevent corresponding side-to-side panning motion of the tube array in the workspace. Finally, first and second roll sensors positioned on the device detect angular motion of handle 100 in a rolling motion about translation axis 118a. If the angular position data acquired by each of the first and second roll sensors is not within a predetermined threshold range of similarity, the system may prevent corresponding rolling motion of the tube array in the workspace. By providing redundant sensors along each axis in some embodiments, inadvertent movement of the tube array in the workspace may be prevented.

Figure 6:
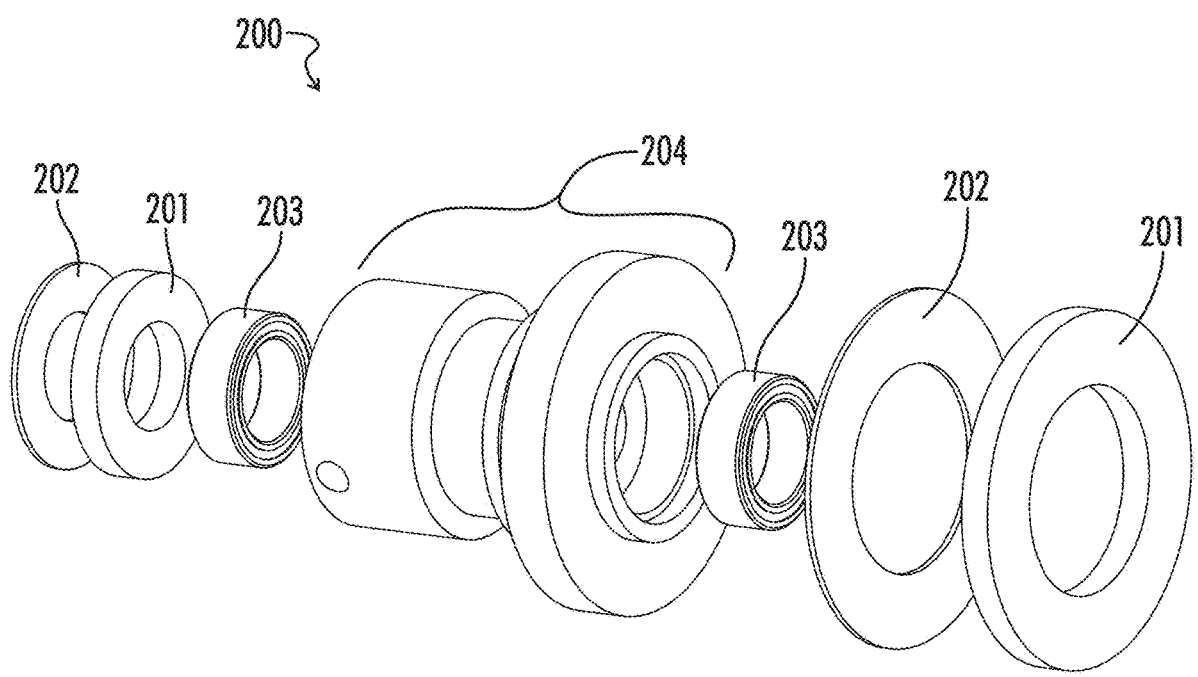
FIG. 6 illustrates an exploded view of the embodiment of a handle bearing assembly in FIG. 3.
Figure 7:
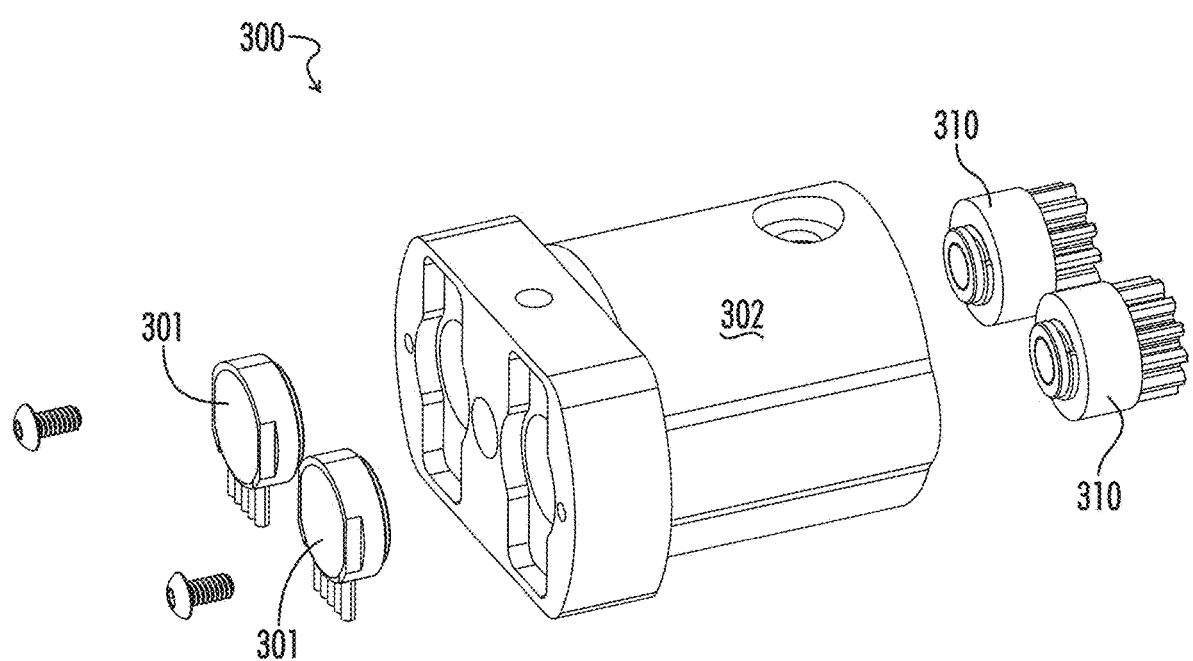
FIG. 7 illustrates an exploded view of the embodiment of a sensor housing assembly in FIG. 3.
Figure 8:
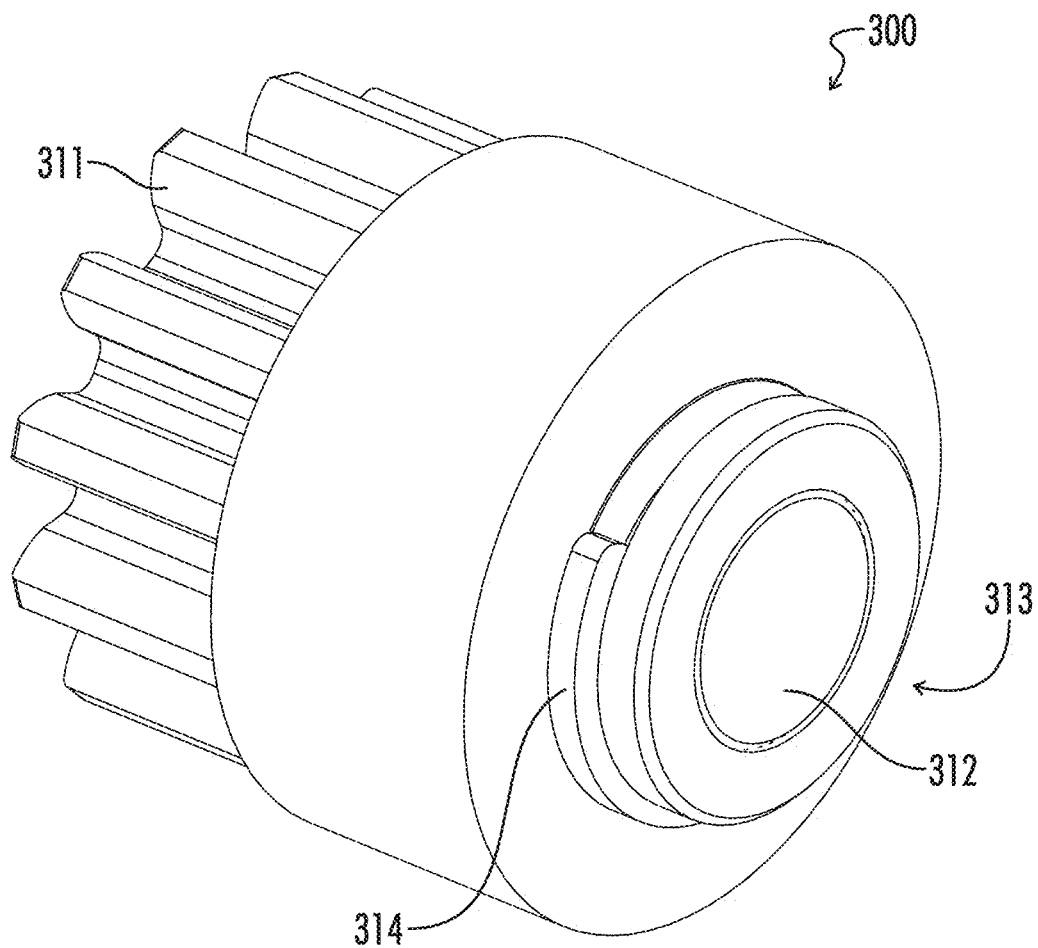
FIG. 8 illustrates a perspective view of the embodiment of a magnet sensor gear assembly as shown in FIG. 7.

Referring to FIG. 6, a handle bearing assembly 200 can be comprised of an interconnected series of flat washers 201, friction gaskets 202, ball bearings 203, and a handle bearing block 204. As shown in FIG. 7, in certain embodiments, magnetic sensor housing assembly 300 comprises a magnetic sensor housing main body 302. Housed within the main body 302 can be a plurality of magnetic rotary encoders 301 attached to a corresponding plurality of magnetic sensor gear assemblies 310. The magnetic sensor gear assembly 310, as shown in FIG. 8, can further comprise a magnet seated gear 311, a magnet 312, a chemical resistant dry running sleeve bearing 313 inside of the magnetic sensor gear assembly, and a retaining ring 314. These features detect rotation of the handle to control corresponding rotation of the tube assembly.

Figure 9:
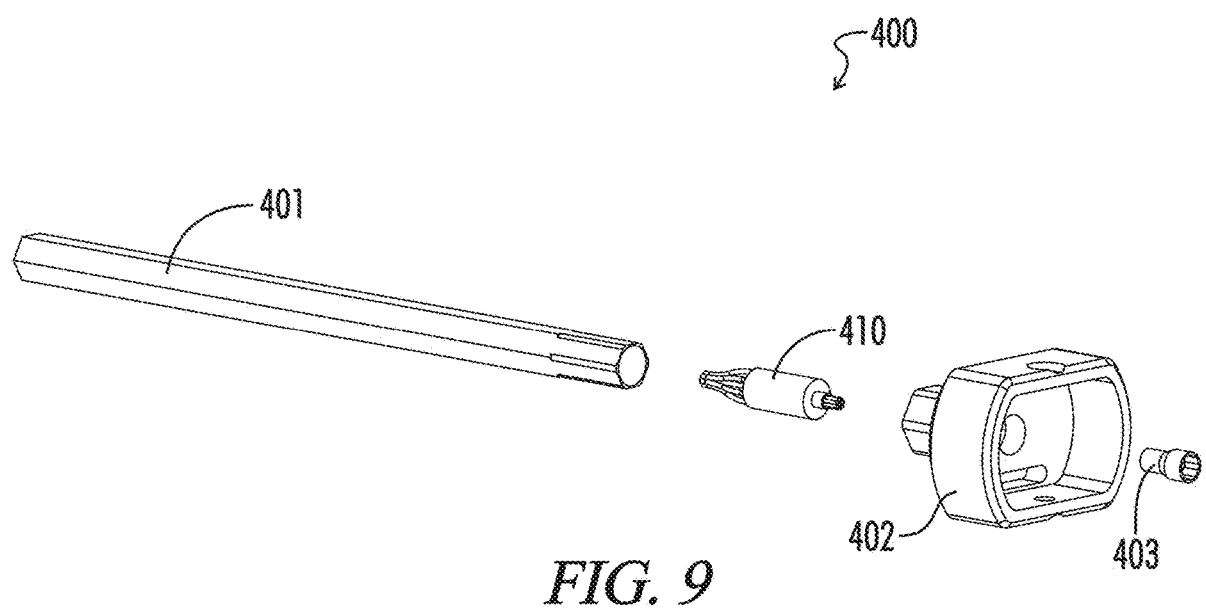
FIG. 9 illustrates an exploded view of the embodiment of a shaft stem assembly as shown in FIG. 3.
Figure 10:
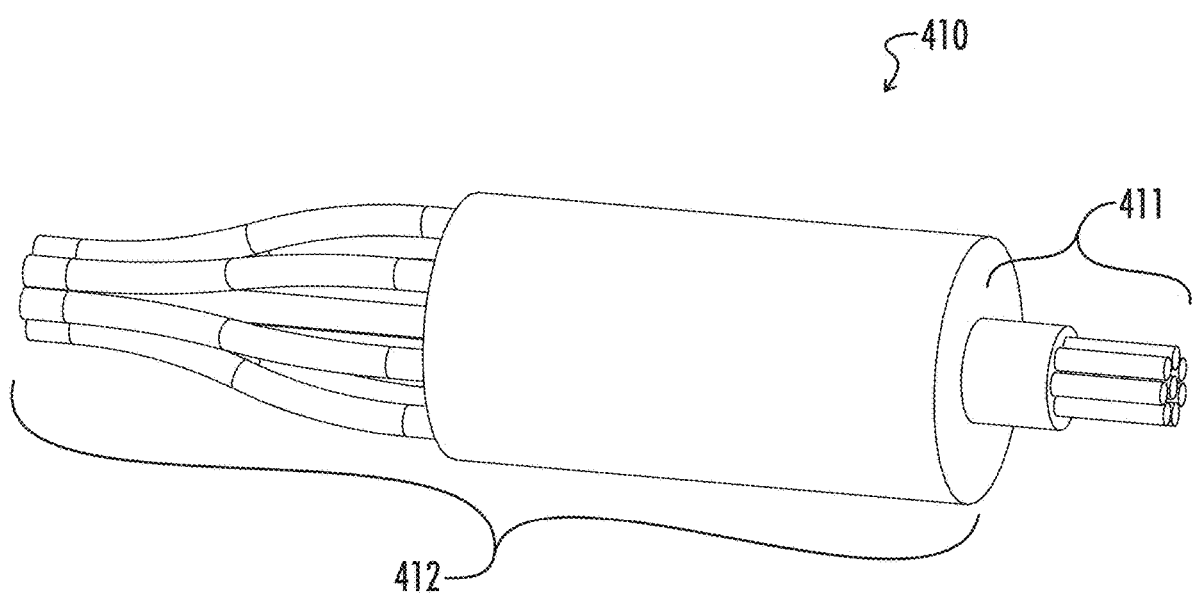
FIG. 10 illustrates a perspective view of the embodiment of a capsule slip ring, as shown in FIG. 9.

Referring to FIGS. 9 and 10, one embodiment of a hex shaft stem assembly 400 can comprise a hex shaft 401, a hex shaft mount 402, a capsule slip ring 410, and a slip ring adapter 403, wherein the capsule slip ring 410 further comprises a rotating slip ring 411 and a stationary slip ring 412. In some embodiments, the slip ring adapter 403 can align with and directly fit around the tip of the touch point shaft 101. In this arrangement, the capsule slip ring 410 can pass conductors to the rotatable touch point assembly 100. Furthermore, in certain embodiments, axial rotation controls have about a one-to-one ratio of corresponding movement in the endoscopic concentric tube robot 2, but such ratio can be scaled up or down in other embodiments as required for particular applications.

Figure 11:
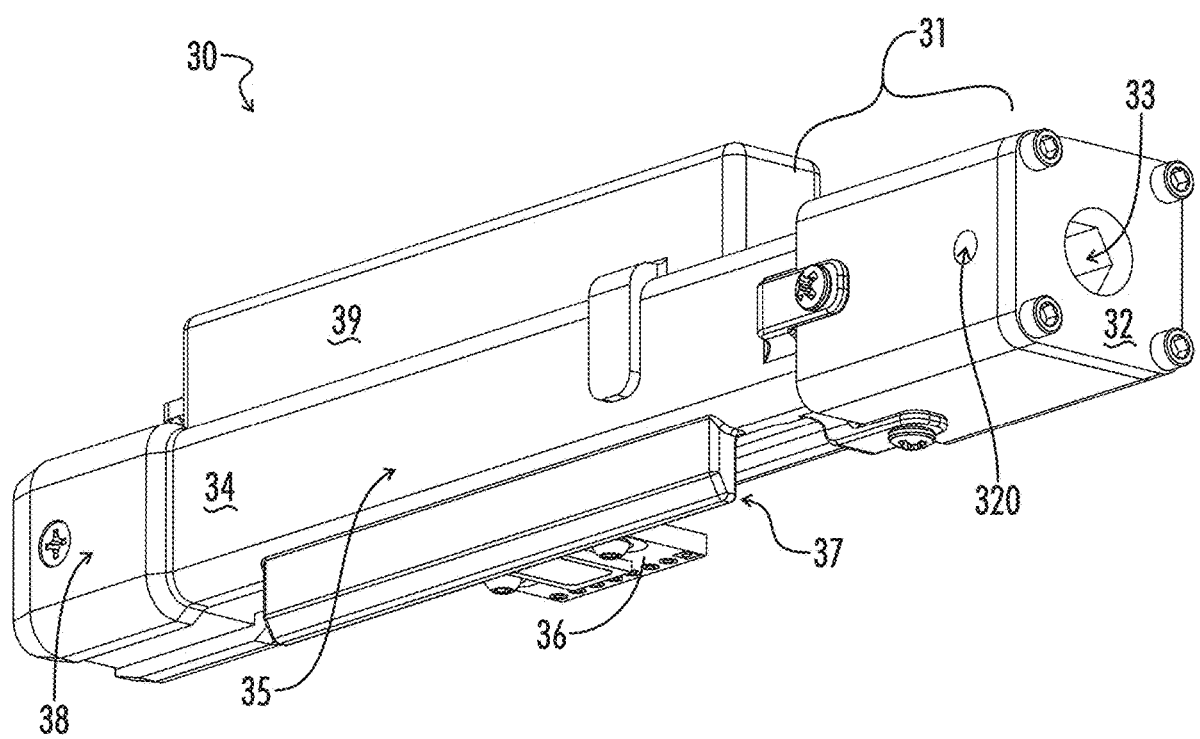
FIG. 11 illustrates a perspective view of the embodiment of a user interface linear joint assembly, as shown in FIG. 2.

As depicted in FIG. 11, one embodiment of a user interface linear joint assembly 30 may comprise an input shaft channel 31, an end cap 32, a plurality of friction bearings 33 lining the inside of the input shaft channel 31, body cover 34, a potentiometer 35 housed inside the body cover 34, an incremental magnetic encoder 36 in direct contact with the potentiometer 35, an MS05-A-L60 37, a counter weight 38 housed inside the second end of the user interface linear joint assembly 30, a body cover extension 39, and a tilt-axis 320 about which the user interface linear joint can pivot up and down. In such an embodiment, the user interface handle assembly 10 is coupled with the user interface linear joint assembly 30 by a mated interconnection between the shaft 401 and the friction bearings 33, wherein the tip of the shaft 401 fits into the potentiometer 35. In this arrangement, the incremental magnetic encoder 36 is capable of sensing when there has been a translation movement in the user interface handle assembly 10, thereby triggering a corresponding translation movement in the tube assembly. The potentiometer 35 provides a first translation sensor, and the incremental magnetic encoder 36 provides a second translation sensor. The first and second translation sensors both detect linear movement of the handle 100 along the translation axis 118a. Although the first and second sensors operate differently, they provide redundant position sensing for the translation of the handle 100, thereby providing a backup safety feature that prevents inadvertent movement of the tube array in the workspace.

In some embodiments, when the user interface handle assembly 10 is translated relative to the linear joint assembly, position data is acquired via first and second translation sensors and a translation control signal is sent to a driver coupled to the tube assembly. The translation control signal may be sent via a wired connection to the driver, or sent via a wireless transceiver or transmitter in some embodiments.

Due to the internal friction bearings 33, there is a noticeable amount of resistance when the physician is moving the handle assembly 10 in translation. Such resistance is a preferred and intentional feature that can help increase patient safety, as surgeons observe that it helps them feel the movements better, almost as if they are moving the tools themselves through the endoscope, and not via a robotic interface. The feeling of resistance along the translation axis could also be created by one or more motors on a low-friction device to provide the feeling of resistance as the handle is translated linearly along the translation axis 118a. Furthermore, in some embodiments, translation controls have about a two-to-one ratio of corresponding movement in the tube assembly, but can be adjusted in other embodiments as necessary.

Figure 12:
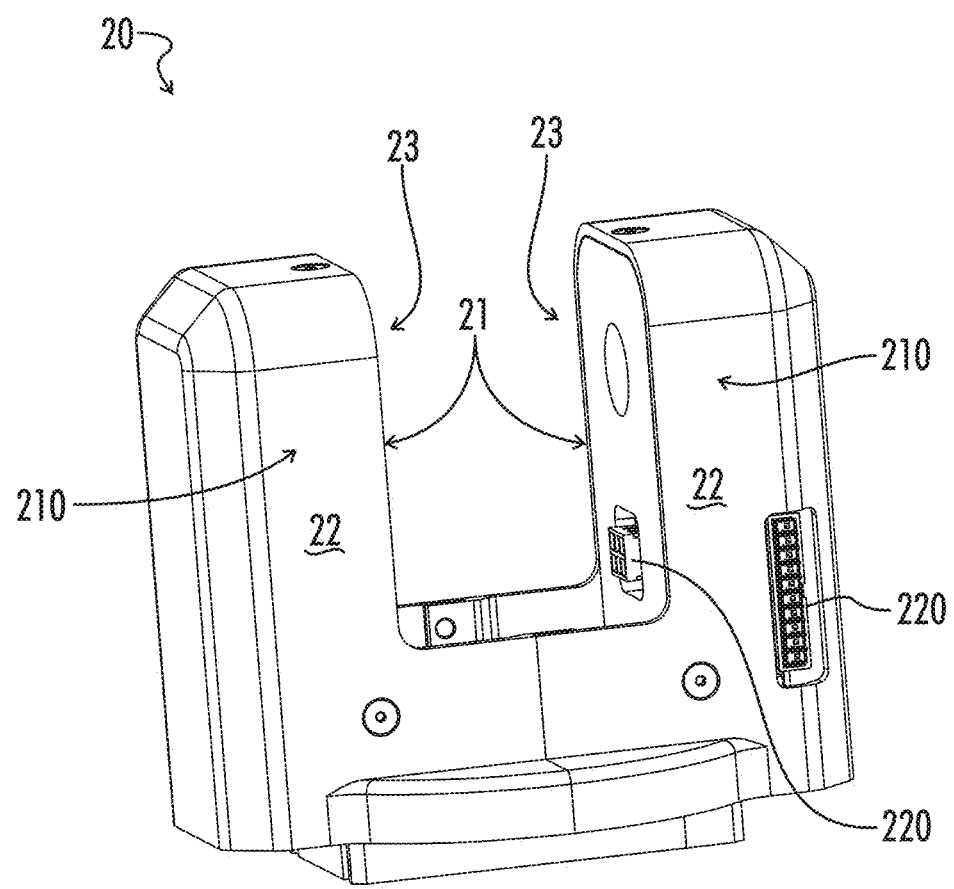
FIG. 12 illustrates a perspective view of the embodiment of a user interface pan/tilt assembly, as shown in FIG. 2.
Figure 13:
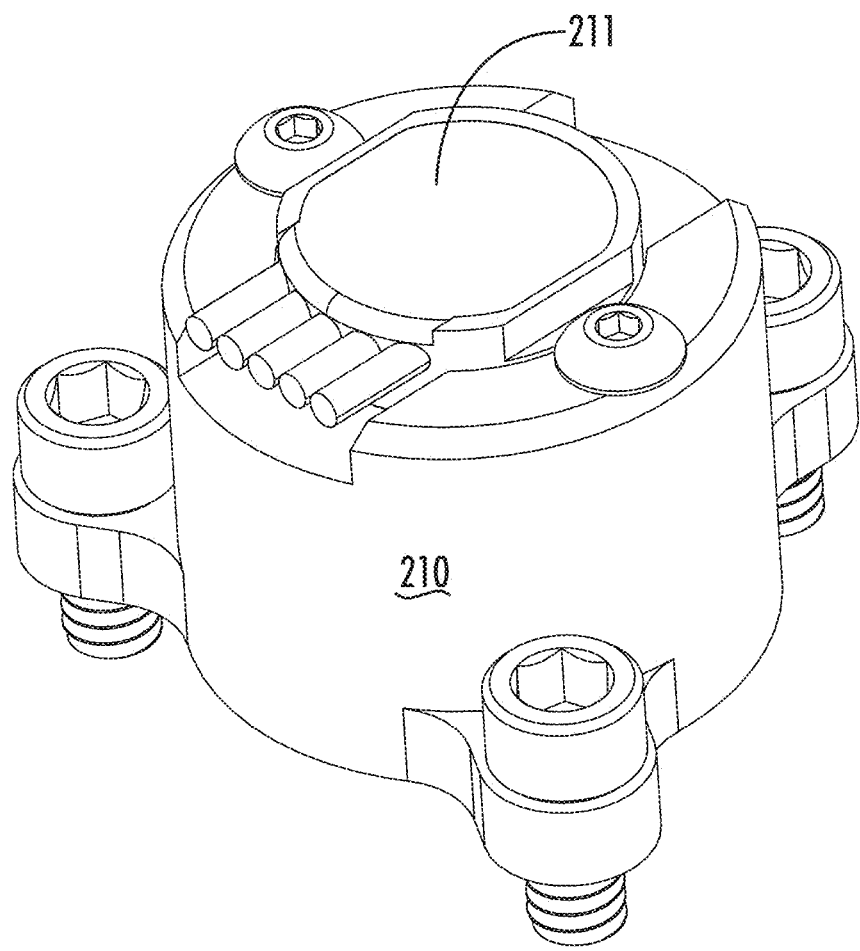
FIG. 13 illustrates a perspective view of the embodiment of a magnetic sensor mount, as depicted in FIG. 12.
Figure 14:
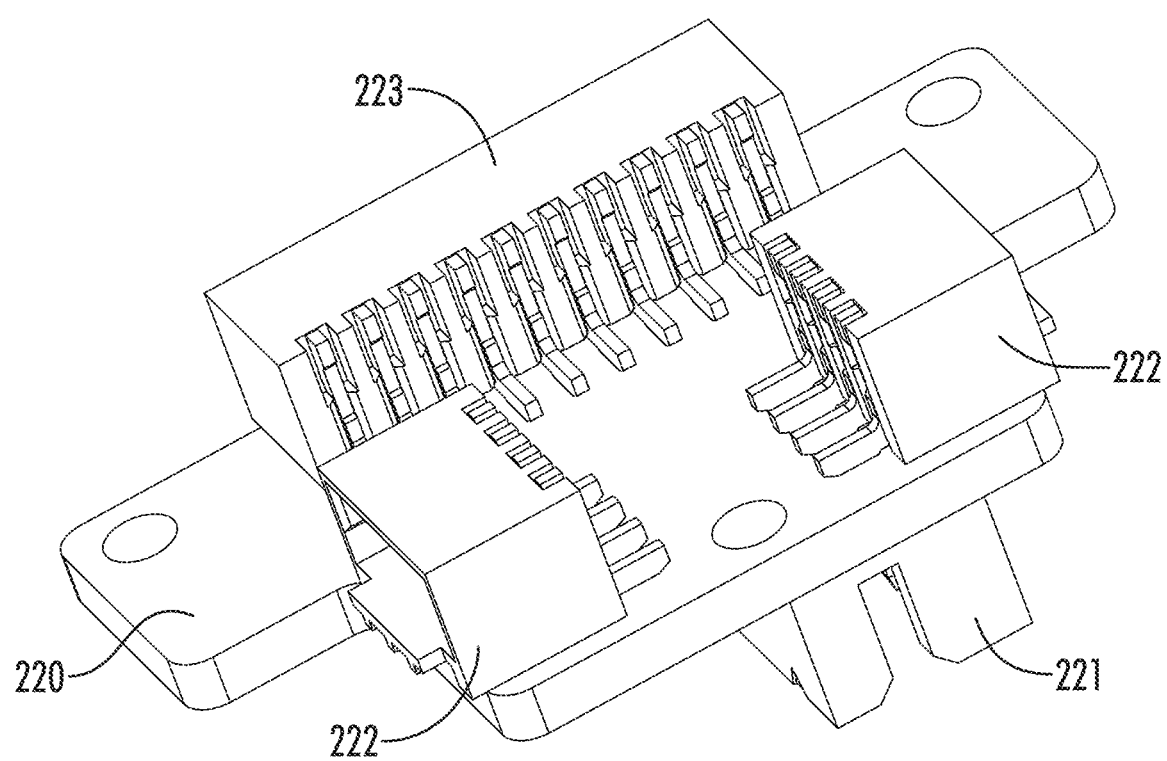
FIG. 14 illustrates a perspective view of the embodiment of a tilt-axis circuit board, as shown in FIG. 12.
Figure 15:
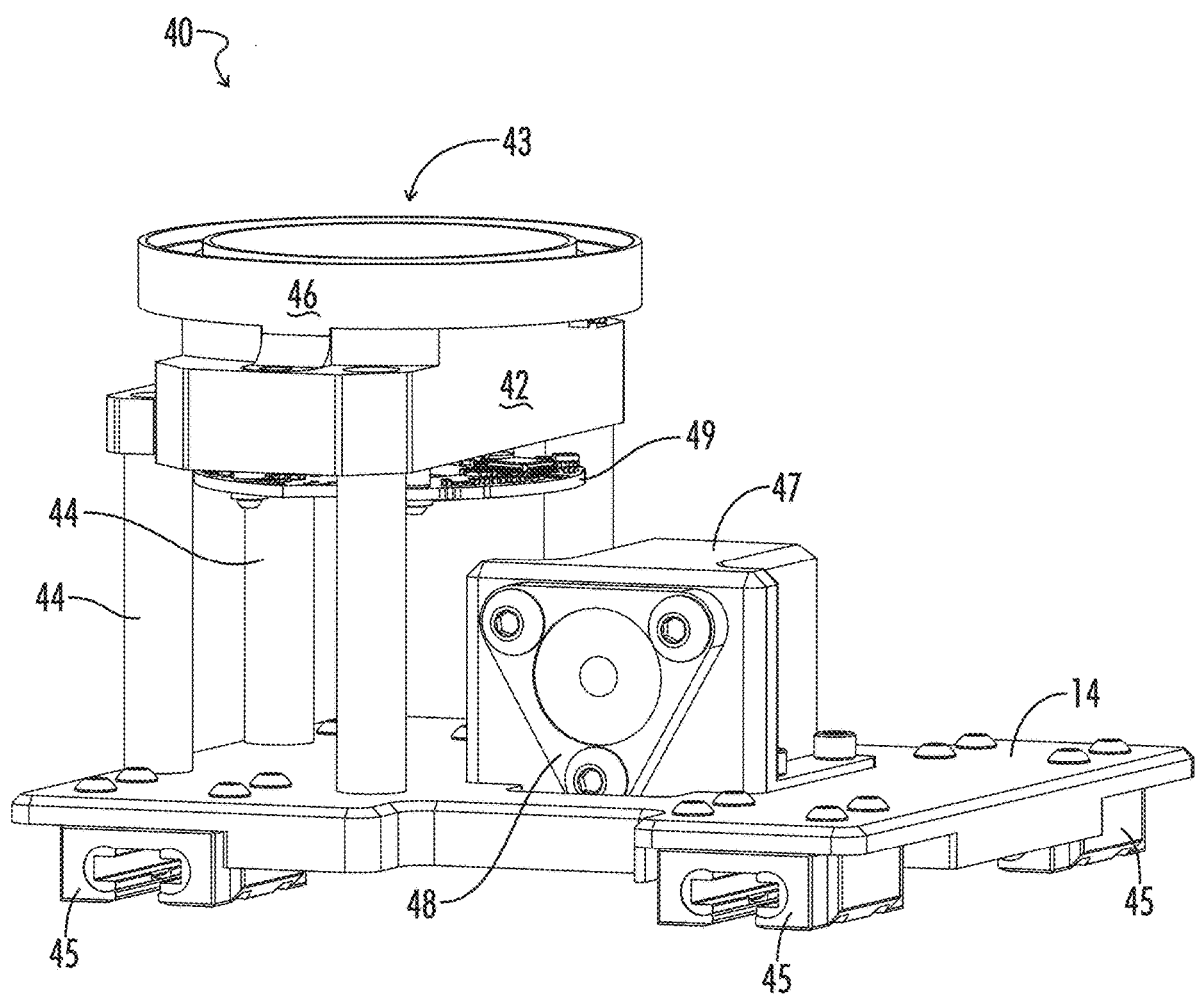
FIG. 15 illustrates a perspective view of the embodiment of a user interface base assembly, as shown in FIG. 2.
Figure 16:
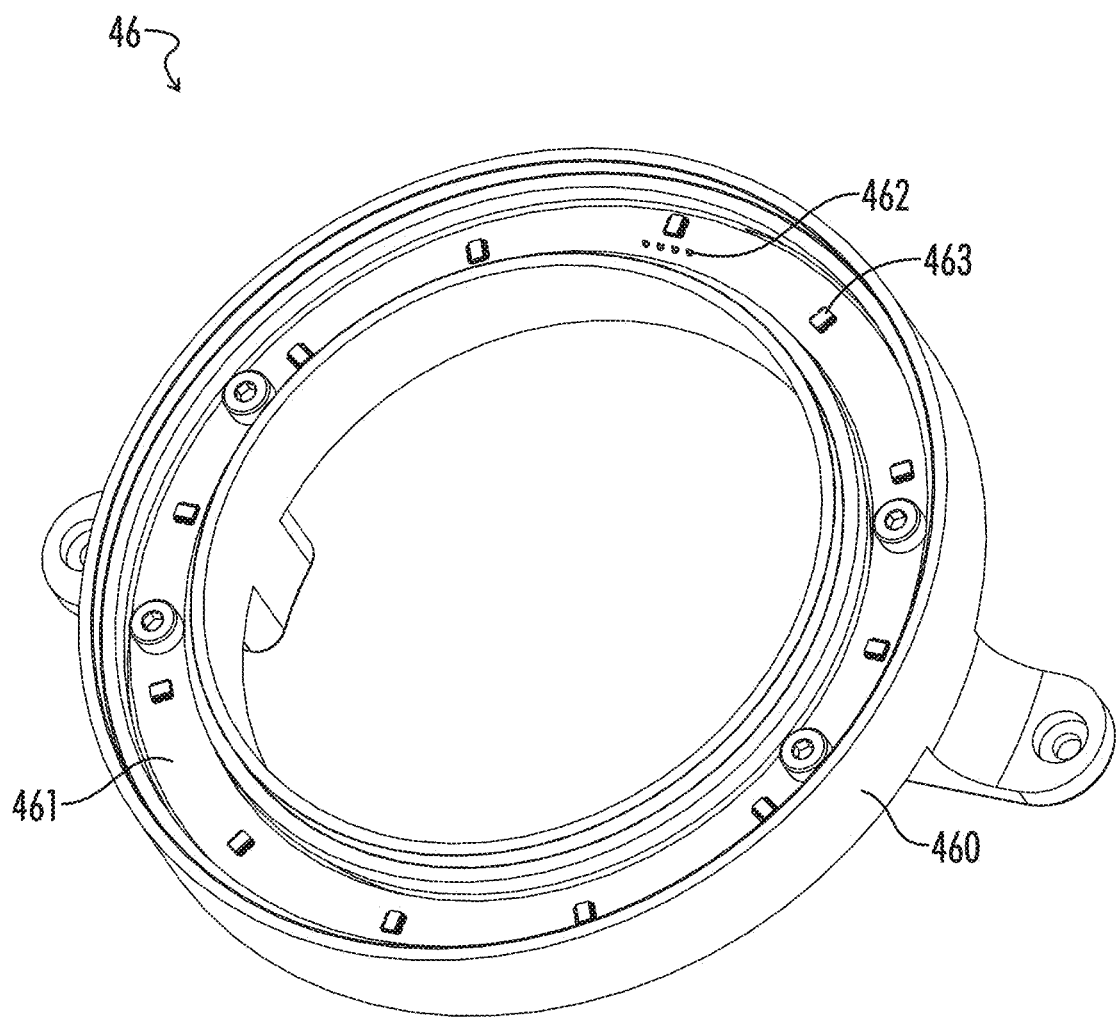
FIG. 16 illustrates a perspective view of the embodiment of a ring LED printed circuit board and housing assembly, as shown in FIG. 15.
Figure 17:
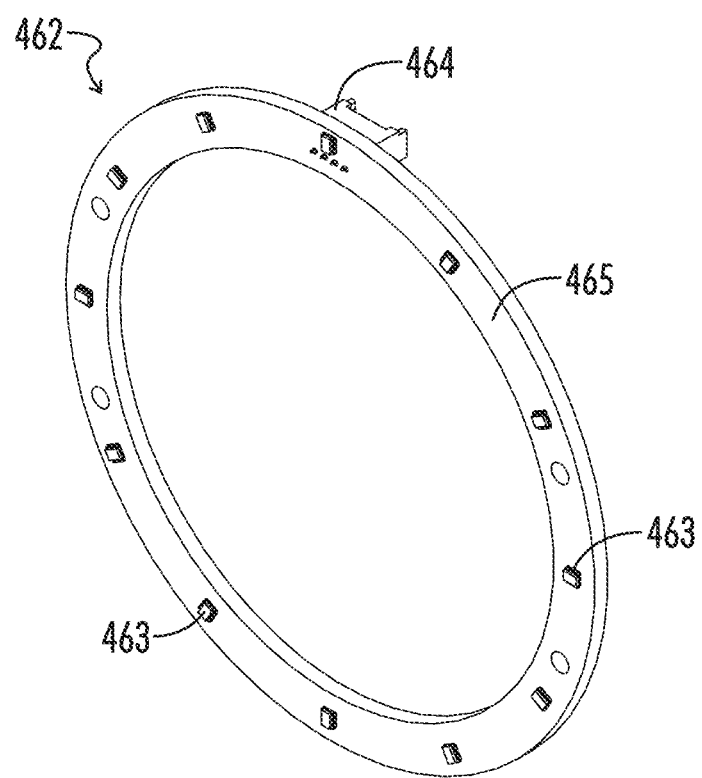
FIG. 17 illustrates a perspective view of the embodiment of the ring LED printed circuit board, as shown in FIG. 16.
Figure 18:
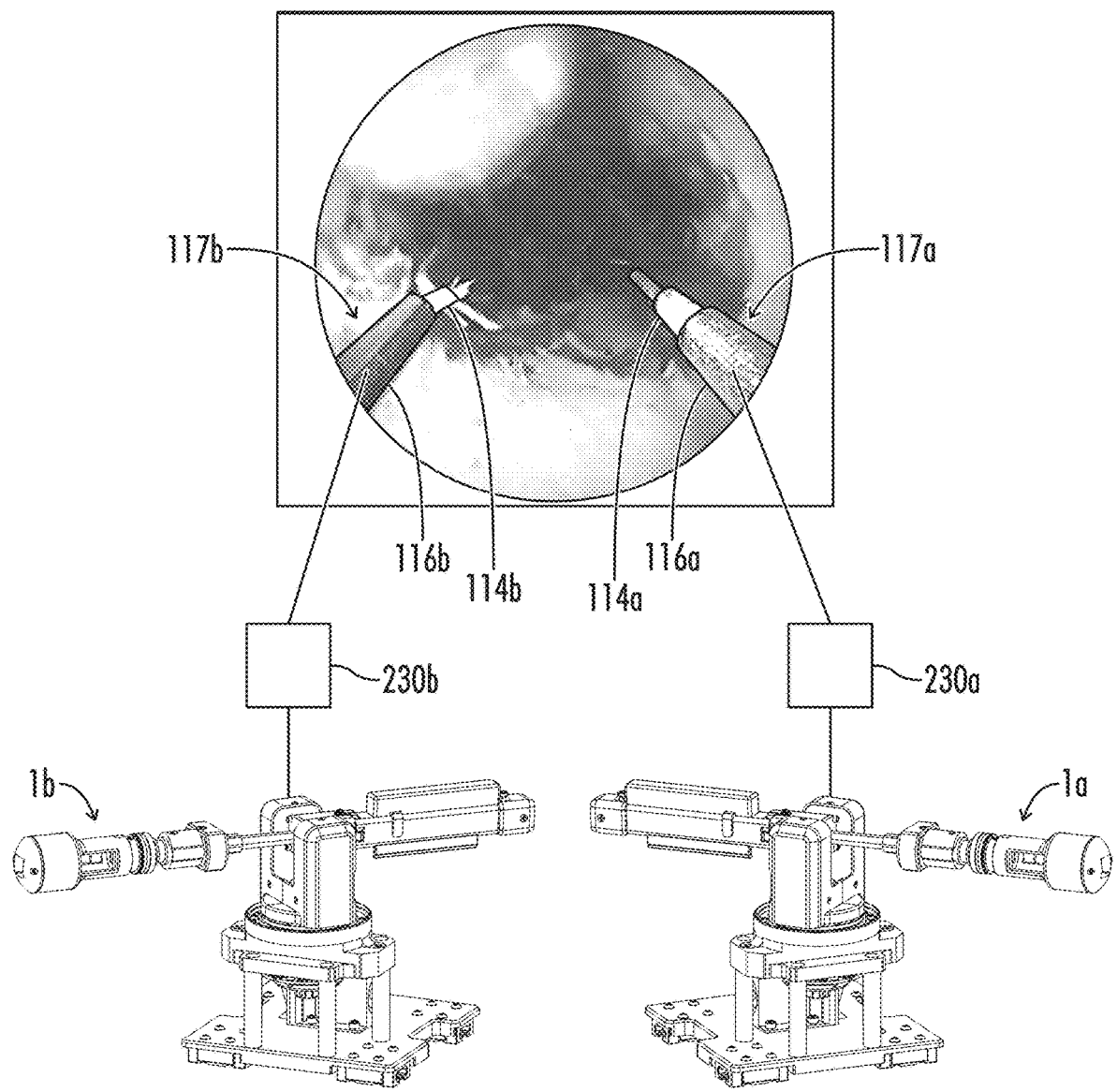
FIG. 18 illustrates a perspective view of an embodiment of a surgery system including first and second input devices and first and second concentric tube assemblies.

Input device 1 further includes a mount, or user interface pan/tilt assembly 20, for providing pan and tilt capabilities. One embodiment of a user interface pan/tilt assembly 20 can be seen in FIGS. 12-14. In this embodiment, the user interface pan/tilt assembly 20 may be U-shaped and comprise two opposing blocks 21 housed within two block covers 22, a stainless steel ball bearing 23 inside each of the blocks 21, a magnetic sensor mount 210 housed inside each of the blocks 21, and a tilt axis circuit board 220 connected to one of the blocks 21. In such an embodiment, each of the magnetic sensor mounts 210 further comprise a magnetic rotary encoder 211; and the tilt axis circuit board 220 further comprises a plurality of connectors for transmitting electrical signals to and from the pan/tilt assembly 20.

Also in such an embodiment, the interconnected user interface handle assembly 10 and user interface linear joint assembly 30 are further connected to the user interface pan/tilt assembly 20 by a pair of tilt axis fasteners which are customized to connect each of the tilt axis 320 portions of the linear joint assembly 30 to each of the two stainless steel ball bearings 23. In this arrangement, the magnetic rotary encoders 211 are capable of sensing when there has been a tilting up or down movement of the interconnected handle/linear joint/pan/tilt assembly about the about the tilt axis 320, thereby triggering a corresponding tilting movement in the tube assembly in the field of view. Furthermore, in certain embodiments, tilting controls have about a one-to-one ratio of corresponding angular movement in the tube assembly, but such ratio can be adjusted up or down in other embodiments as necessary.

An embodiment of a user interface base assembly 40 can be seen illustrated in FIGS. 15-19. In some embodiments, the user interface base assembly may comprise a base plate 41, a base housing 42 elevated above the base plate 41 by a plurality of spacer legs 44, two ball bearings 43 aligned on top of one another and contained inside the base housing 42, a plurality of sleeve bearing carriages mounted to the bottom side of base plate 41, a ring LED assembly 46 mounted on top of the base housing 42, a lead nut housing 47 mounted on the top side of base plate 41, a lead nut (or equivalent) 48 contained within the lead nut housing 47, and an off-axis rotary absolute magnetic encoder 49 mounted to the bottom of the base housing 42. In such embodiments, the ring LED assembly 46 comprises a ring LED housing 460, a ring LED cover 461, and a SW LED ring 462; the SW LED ring 462 can further comprise a ring LED printed circuit board 465

As can be seen in the embodiment of the physician input device 1 within FIG. 2, a redundant off-axis rotary absolute magnetic encoder 50, comprising an elastoferrite top ring layer 51 and a bottom ring layer, is mounted to the bottom of the base housing 42 in a position further below encoder 49. In such an embodiment, the user interface base assembly 40 is interconnected with the U-shaped user interface pan/tilt assembly 20 by means of a "main shaft" that runs from the base of the U-shaped pan/tilt assembly 20 down through the ring LED assembly 46, stacked ball bearings 43, and the base housing 42 of base assembly 40. In this embodiment, the user interface handle assembly 10, U-shaped user interface pan/tilt assembly 20, user interface linear joint 30, user interface base assembly 40, and redundant off-axis rotary absolute magnetic encoder 50 form one interconnected unit. In this arrangement, the off-axis rotary absolute magnetic encoder 49 and redundant off-axis rotary absolute magnetic encoder 50 are capable of sensing when there has been a panning side-to-side movement of the interconnected handle/linear joint/pan/tilt assembly about the "main shaft," thereby triggering a corresponding panning movement in the tube assembly. Furthermore, in certain embodiments, panning controls have about a one-to-one ratio of corresponding movement in the tube assembly, but such ratio can be adjusted up or down in other embodiments as necessary.

The rotary encoder detects angular position of the user interface pan/tilt assembly 20 as it rotates relative to user interface base assembly 40 about reference vertical axis 118c and generates a position signal. The position signal is used to generate a pan control signal that is transferred to a driver to cause a corresponding side-to-side pan motion in tube assembly. The pan control signal may be sent via a wired or a wireless connection to the driver. In some embodiments, the pan signal transmitted from the user interface 1 includes angular position data acquired via rotary encoder 50. In other embodiments, the pan signal transmitted from the user interface 1 includes additional components calculated to drive corresponding motion of the tube assembly.

In some embodiments, the user input device 1 provides a translation stroke of about 50 mm to about 60 mm. This range can be adjusted up or down depending on the application. A stroke distance in this range provides a corresponding stroke range of the inner tube 114 of about 30 mm to about 40 mm in some embodiments. The ratio of input motion at handle 100 to effective motion of the inner tube 114 along each degree of freedom may be adjusted as a software-based gain factor that can be precisely controlled to adjust the sensitivity of the device in some embodiments.

User interface 1 provides a pan/tilt pivot point that is fixed in three-dimensional space due to the interface being mounted on a stationary console or stand. Such a configuration provides a desirable feel to surgeons, where the surgeon is tilting their tool against a constrained center of motion. This layout creates a similar experience to manipulating/tilting tools manually through a port in the patient's body wall during laparoscopic surgery. The pivot point can be enforced mechanically via a pan/tilt gimbal, or in other embodiments the pivot point can be enforced electronically via a haptic system.

Another feature of the user interface 1 provides a system that does not require a "clutch" when the tip 115 is desired to be moved. Because the entire workspace of the tube assembly manipulator is contained within the available range of motion and workspace of the input device, there is no need to decouple the user input from the tube assembly during a surgical operation to re-position the user input as required in other conventional surgical robotic inputs.

A further feature of the user interface 1 provides a system that can be easily calibrated, or homed to a zero position, at the beginning of a procedure. At the beginning of a surgical procedure, when the guide tube 116 and inner tube 114 are fully retracted, the handle 100 may also be manually retracted along the translation axis to the mechanical limit. From this position, the tube assembly and the handle 100 may both be translated forward along the translation axis into the field of view and into the workspace cone defined by the available range of motion of the tube assembly. As such, alignment of the handle 100 with the tube assembly may be easily enforced at the beginning of each operation.

Referring further to FIG. 21, in some embodiments, a surgery system includes a first input device 1a and a second input device 1b. First input device 1a is configured to acquire linear translation, pan and tilt data associated with movement of a handle. The acquired data is communicated via a wired or wireless interface to a first driver 230a that is mechanically linked to a first concentric tube array 117a. First driver 230a controls motion of the first concentric tube array 117a in a field of view corresponding to the position data acquired by the first input device 1a. Second input device 1b is configured to acquire linear translation, pan and tilt data associated with movement of the handle on second input device 1b. The acquired data is communicated via a wired or wireless interface to a second driver 230b that is mechanically linked to a second concentric tube array 117b. Second driver 230b controls motion of the second concentric tube array 117b in a field of view corresponding to the position data acquired by the second input device 1b.

In further embodiments, the present disclosure provides a method of controlling a concentric tube assembly for performing surgery. The method includes the steps of: (a) providing a user input with three degrees of freedom, including translation, tilt and pan; (b) acquiring linear position data representative of translation of a user input device relative to a linearly fixed frame of reference; (c) acquiring tilt angular position data corresponding to angular movement about a fixed horizontal reference axis; (d) acquiring pan angular position data corresponding to angular movement about a fixed vertical reference axis; (e) mapping the acquired linear position data, tilt angular position data and pan angular position data onto corresponding movement of surgical tool in a remote concentric tube array.

In some embodiments, the method further includes providing a handle on the user input including a first sensor and a second sensor, wherein the device is inoperable unless the first and second sensors are both activated. In some embodiments the first and second sensors are capacitive touch sensors.

In some embodiments, the method further includes providing a first user input device configured for use by a user's right hand, and a second user input device configured for use by a user's left hand. The first and second user input devices are each connected electronically to respective first and second concentric tube assemblies for performing surgery. Each user input device includes at least three degrees of freedom, including linear translation, pan and tilt, and movement of each device causes corresponding movement in the respective concentric tube array along each degree of freedom.

Figure 19:
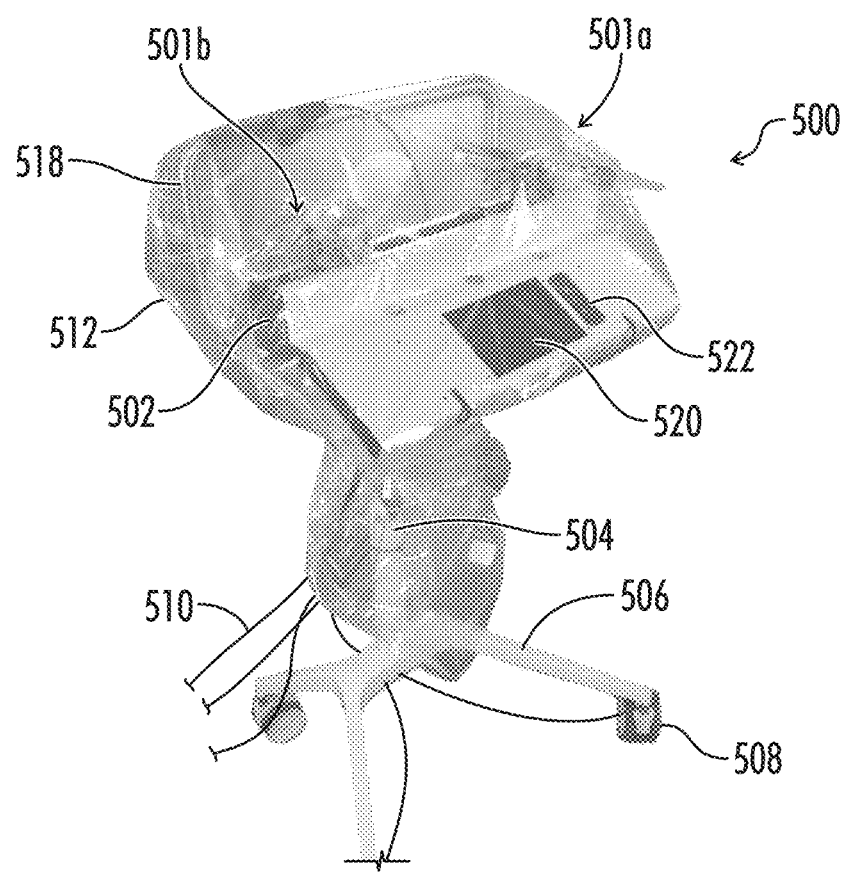
FIG. 19 illustrates a perspective view of an embodiment of a physician input console including first and second physician input devices.
Figure 20:
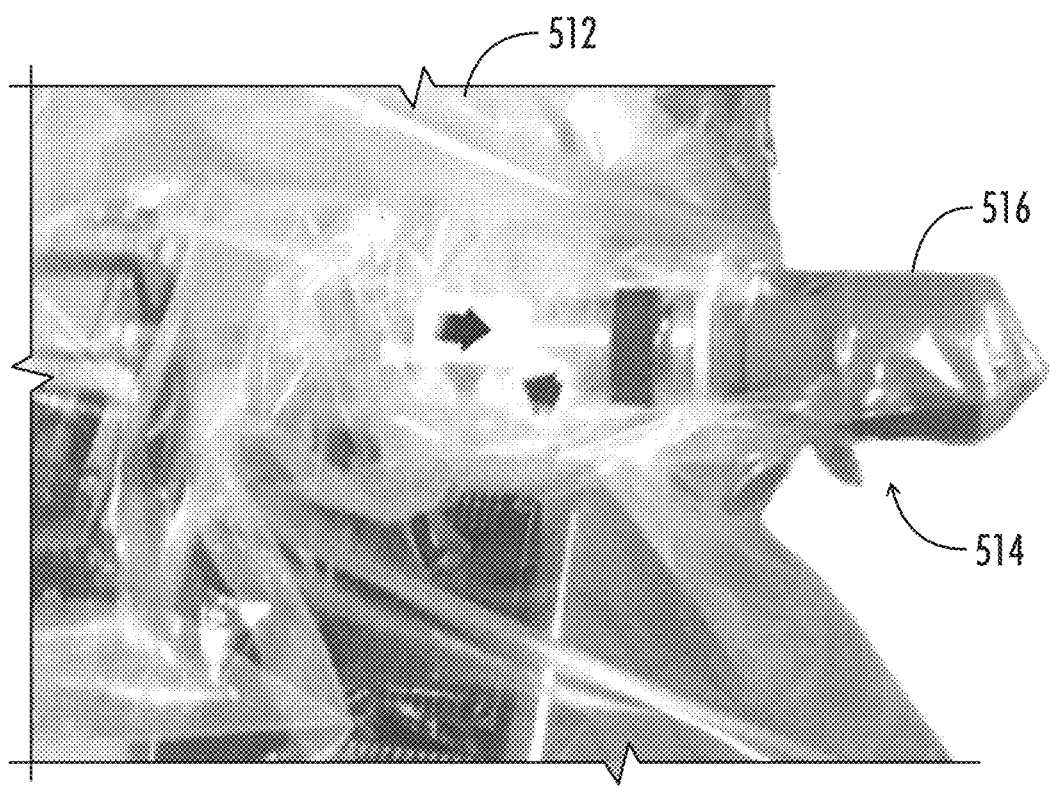
FIG. 20 illustrates a detail perspective view of an embodiment of a physician input device with a surgical drape.

Referring to FIGS. 19-20, in some embodiments, a surgeon input console 500 includes a first user input device 501a and a second user input device 501b. First and second input devices 501a, 501b are mounted on a frame 502. In some embodiments, frame 502 is configured such that the distance between first and second input devices 501a, 501b is variable and may be adjusted to accommodate surgeons with different physical attributes, such as a shorter or longer arms and/or different hand sizes. Frame 502 is positioned atop a shaft 504 extending upwardly from a base 506. Frame 502 includes a user display screen 520 and a user control panel 522 in some embodiments. Shaft 504 is selectively extendable in some embodiments to accommodate surgeons in a sitting or standing position, or to accommodate surgeons of different heights or arm lengths. Base 506 includes a plurality of wheels disposed thereon such that the console 500 may be rolled on a hard surface such as a hospital floor. A plurality of wires 510 extend from the console 500 to a surgical apparatus including a concentric tube assembly for performing surgery. The wires 510 transmit signals back and forth between the surgical apparatus and the console 500. In some embodiments, communication between the surgical apparatus and the console 500 is via wireless communications.

As shown in FIGS. 19 and 20, in some embodiments, console 500 is specially adapted for use with a surgical drape 512. Drape 512 provides a sterile barrier, allowing console 500 to be used in a surgical field in an operating room. Drape 512 covers the console 500, frame 502, first and second user input devices 501a, 501b and shaft 504 in some embodiments. Each user input device 501a, 501b is specifically designed such that a surgeon can manually operate the device while fitted with a surgical drape.

For example, as shown in FIG. 19, console 500 includes a drape support 518 extending upwardly above the frame 502, and also extending upwardly above first and second user input devices 501a, 501b in some embodiments. Drape support 518 includes a horizontal bar spanning at least the distance between the first and second user input devices 501a, 501b and offset on the side of the first and second user input devices 501a, 501b away from the display screen 520 in some embodiments. Drape support 518 allows the drape 512 to form a tent over the input devices 501a, 501b such that the input devices may move in a relatively free range of motion inside the tent formed by drape 512. Drape 512 is generally loose-fitting over the console such that the user input devices may be freely manipulated and repositioned on the frame if necessary. Drape 512 may be secured to the console 500 using one or more fasteners, such as tape or magnets, to secure the drape 512 in a desired position on the console 500.

Also, as shown in FIG. 20, a drape 512 including a pocket 514 may be fitted over a handle 516 on a user input device 501a. Due to the mechanical configuration of the user input device handle, pan and tilt assembly and base assembly, a surgeon may still achieve manipulation of the handle 516 along all degrees of freedom, including rotation, when the device is fitted with a drape 512. This configuration of the input device makes usage of the device in a surgical field possible. For example, in some embodiments, drape 512 includes a pocket 514 that is separate from the main body of the drape 512 around handle 516, such that handle 516 may rotate freely along with its independent pocket 514. A seal is provided between the pocket 514 and the drape body 512 to prevent contamination in some embodiments. Additionally, the drape 512 may be secured to the shaft 504 using a fastener such as tape to secure the lower end of the drape 512 to the console.

Thus, although there have been described herein particular embodiments of the present invention of new and useful physician input devices for the control of concentric tube robots during minimally invasive surgery, it is not intended that such references be construed as limitations upon the scope of this invention except as set forth in the following claims.

What is claimed is:

1. An input apparatus for controlling a concentric tube assembly, comprising:
 a linear joint assembly including a bore and a linear encoder;
 a user input assembly including a handle and a shaft extending from the handle into the bore, wherein the shaft is moveable relative to the linear encoder along a linear translation axis, and wherein the linear encoder acquires translation position data representative of the linear position of the shaft relative to the linear joint assembly;
 a pan and tilt assembly supporting the linear joint assembly, wherein the linear joint assembly is pivotable relative to the pan and tilt assembly about a reference horizontal axis; and
 a base assembly supporting the pan and tilt assembly, wherein the pan and tilt assembly is rotatable relative to the base assembly about a reference vertical axis,
 wherein the handle is moveable in at least three degrees of freedom relative to the base assembly.

2. The apparatus of claim 1, further comprising:
 a tilt sensor disposed between the linear joint assembly and the pan and tilt assembly, wherein the rotation sensor acquires tilt position data representative of the angular position of the linear joint assembly relative to the pan and tilt assembly about the horizontal reference axis.

3. The apparatus of claim 2, further comprising:
 a pan sensor disposed between the pan and tilt assembly and the base assembly, wherein the rotation sensor acquires pan position data representative of the angular position of the pan and tilt assembly relative to the base assembly about the vertical reference axis.

4. The apparatus of claim 3, further comprising:
 a concentric tube array comprising a guide tube and an inner tube housed inside the guide tube, wherein the inner tube is translatable relative to the guide tube.

5. The apparatus of claim 4, wherein the concentric tube array is coupled electronically to the input device such that movement of the input device causes corresponding motion in the concentric tube array via the translation position data, tilt position data and pan position data.

6. A physician input device for controlling a concentric tube assembly, comprising:
 a user interface handle assembly having a first and second end;
 a user interface linear joint assembly;
 a user interface pan and tilt assembly, wherein the linear joint assembly is pivotable relative to the pan and tilt assembly about a reference horizontal axis;
 a user interface base assembly, wherein the pan and tilt assembly and linear joint assembly are pivotable relative to the base assembly about a reference vertical axis.

7. The device of claim 6, further comprising:
 a linear encoder disposed on the linear joint assembly, wherein the linear encoder is configured to output a translation position signal representative of the position of the user interface handle assembly.

8. The input device of claim 7, wherein the user interface handle assembly further comprises:
 a touch point assembly, located at the first end of the user interface handle assembly;
 a handle bearing assembly; and
 a shaft stem assembly extending along a linear translation axis, located at the second end of the user interface handle assembly.

9. The input device of claim 8, wherein:
 the touch point assembly further comprises a touch sensing user interface assembly located at the first end of the user interface handle assembly.

10. The input device of claim 9, wherein the user interface linear joint assembly further comprises:
a translation sensor for detecting movement of the shaft along the translation axis.

11. The input device of claim 10, wherein the user interface handle assembly is connected to the user interface linear joint assembly by a mating interconnection with the shaft located at the second end of the user interface handle assembly.

12. The input device of claim 11, wherein the user pan and tilt assembly is pivotally attached to the user linear joint assembly such that the angle of the shaft may be tilted up and down about a reference horizontal axis, and is also pivotally mounted on the user interface base assembly such that the angle of the shaft may be panned from side to side about a reference vertical axis.

13. The input device of claim 12, wherein the user interface base assembly further comprises:
a base plate;
at least one rotation sensor configured to measure the angular position of the pan and tilt assembly relative to the base assembly; and
an indicator light.

14. The input device of claim 13, wherein base assembly includes first and second pan sensors that each independently detects angular position of the pan and tilt assembly relative to the base assembly.

15. The input device of claim 14, wherein the user interface base assembly is stationary relative to the pan and tilt assembly as the pan and tilt assembly rotates about a reference vertical axis.

16. The input device of claim 15, wherein the fully interconnected user interface handle, linear joint, pan and tilt assembly, and base assembly provide signals for controlling a concentric tube assembly.

17. The input device of claim 16, wherein the input device is configured such that angular rotation of the handle causes a corresponding rotation in the concentric tube assembly.

18. The input device of claim 17, wherein the translation sensor of the user interface linear joint assembly is capable of sensing a translation movement of the shaft sliding along the translational axis and thereby triggering a corresponding translational movement in the concentric tube assembly.

19. The input device of claim 18, wherein the tilt sensor of the pan and tilt assembly is operable to sense a tilting up or down movement about the tilt axis in the interconnected user interface handle and linear joint assembly and thereby trigger a corresponding tilting movement in the concentric tube assembly.

20. The input device of claim 19, wherein the pan sensor of the user interface base assembly is operable to sense a panning side-to-side movement of the pan and tilt assembly about a reference vertical axis and thereby trigger a corresponding panning movement in the concentric tube assembly.

21. A method of controlling a concentric tube assembly for performing robotic surgery, comprising:
(a) providing a user input device including a base, a bearing block pivotally attached to the base and rotatable relative to the base about a vertical reference axis; a linear joint pivotally attached to the bearing block about a horizontal reference axis, and a handle linearly translatable relative to the linear joint, wherein the device includes a linear encoder between the handle and the linear joint, a first rotation sensor between the bearing block and the linear joint, and a second rotation sensor between the base and the bearing block;
(b) acquiring translation data from the linear encoder, tilt angular position data from the first rotation sensor, and pan angular position data from the second rotation sensor;
(c) generating a control signal based on the acquired translation data, tilt angular position data and pan angular position data;
(d) transmitting the control signal to a driver coupled to the concentric tube assembly;
(e) controlling motion of the concentric tube assembly in a field of view via the driver such that the motion of the concentric tube assembly in the field of view corresponds to the motion of the user input device along three degrees of freedom.

22. The method of claim 21, further comprising:
(f) translating the handle toward the linear joint; and
(g) simultaneously extending the inner tube of the tube assembly away from the guide tube into the field of view.

23. The method of claim 21, further comprising:
(f) covering the user input device in a surgical drape; and
(g) operating the user input device in a surgical field.

\* \* \* \* \*